(12) United States Patent
Mori et al.

(10) Patent No.: US 7,553,936 B2
(45) Date of Patent: Jun. 30, 2009

(54) ANTI-TREM-LIKE TRANSCRIPT-1 (TLT-1) ANTIBODIES AND COMPOSITIONS

(75) Inventors: Toshiyuki Mori, Osaka (JP); Daniel W. McVicar, Charles Town, WV (US); Barbara Giomarelli, Frederick, MD (US); A. Valance Washington, Bayamon, PR (US)

(73) Assignee: The United States of America as represented by Secretary Department of Health and Human Services, Washington, DC (US)

( * ) Notice: Subject to any disclaimer, the term of this patent is extended or adjusted under 35 U.S.C. 154(b) by 31 days.

(21) Appl. No.: 11/634,331

(22) Filed: Dec. 4, 2006

(65) Prior Publication Data

US 2008/0131423 A1    Jun. 5, 2008

(51) Int. Cl.
*C07K 16/00* (2006.01)
*C07K 16/46* (2006.01)
*C07K 16/28* (2006.01)
*A61K 39/00* (2006.01)
*A61K 39/395* (2006.01)

(52) U.S. Cl. ............ 530/387.3; 530/387.1; 530/388.22; 530/388.25; 424/130.1; 424/133.1; 424/135.1; 424/143.1; 435/410

(58) Field of Classification Search .................. None
See application file for complete search history.

(56) References Cited

U.S. PATENT DOCUMENTS

2004/0180409 A1    9/2004   McVicar et al.

FOREIGN PATENT DOCUMENTS

WO        WO 02/06329        1/2002

OTHER PUBLICATIONS

Bird et al., Science 1988, 242:423-426.*

* cited by examiner

*Primary Examiner*—Phillip Gambel
*Assistant Examiner*—Sharon Wen
(74) *Attorney, Agent, or Firm*—Edwards Angell Palmer & Dodge LLP; Peter F. Corless; Jonathan M. Sparks

(57) ABSTRACT

The present invention relates to methods and compositions for modulating platelet activity, and methods and compositions for treating a disease or disorder associated with platelet activity in a subject, comprising administering a single chain anti-TREM-like transcript-1 (TLT-1) antibody or a functional fragment or variant thereof in an amount effective to modulate platelet activity.

6 Claims, 13 Drawing Sheets

A
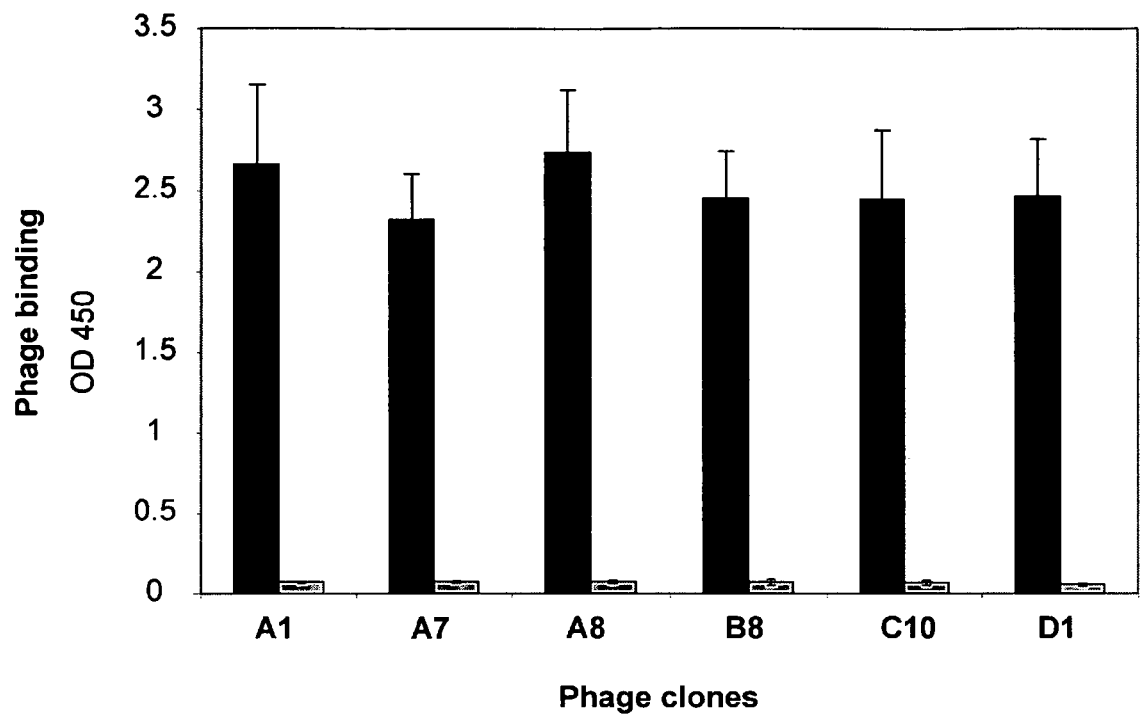
B
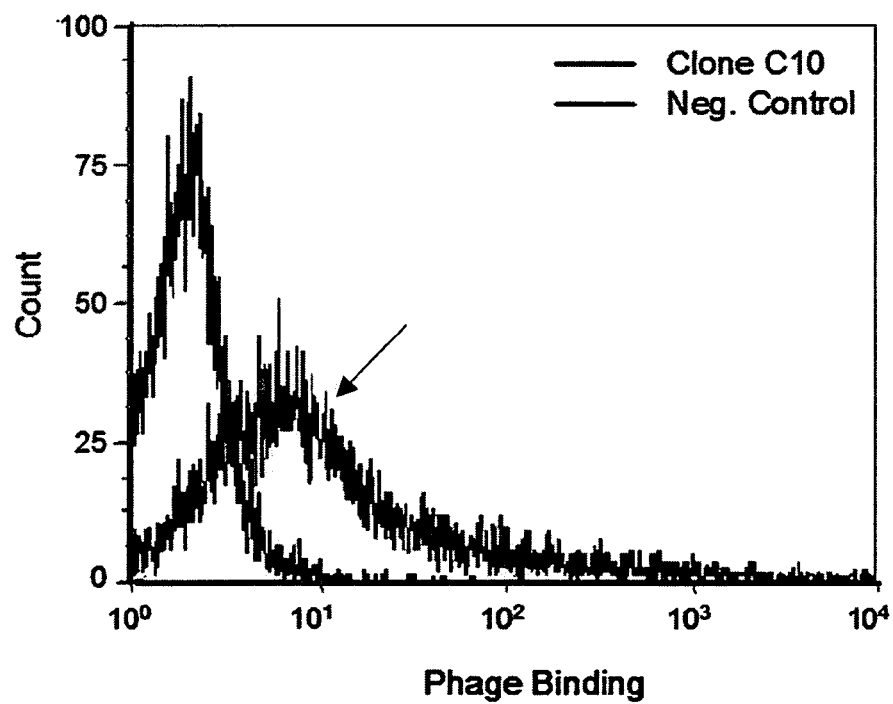
Figure 2 (1/2)

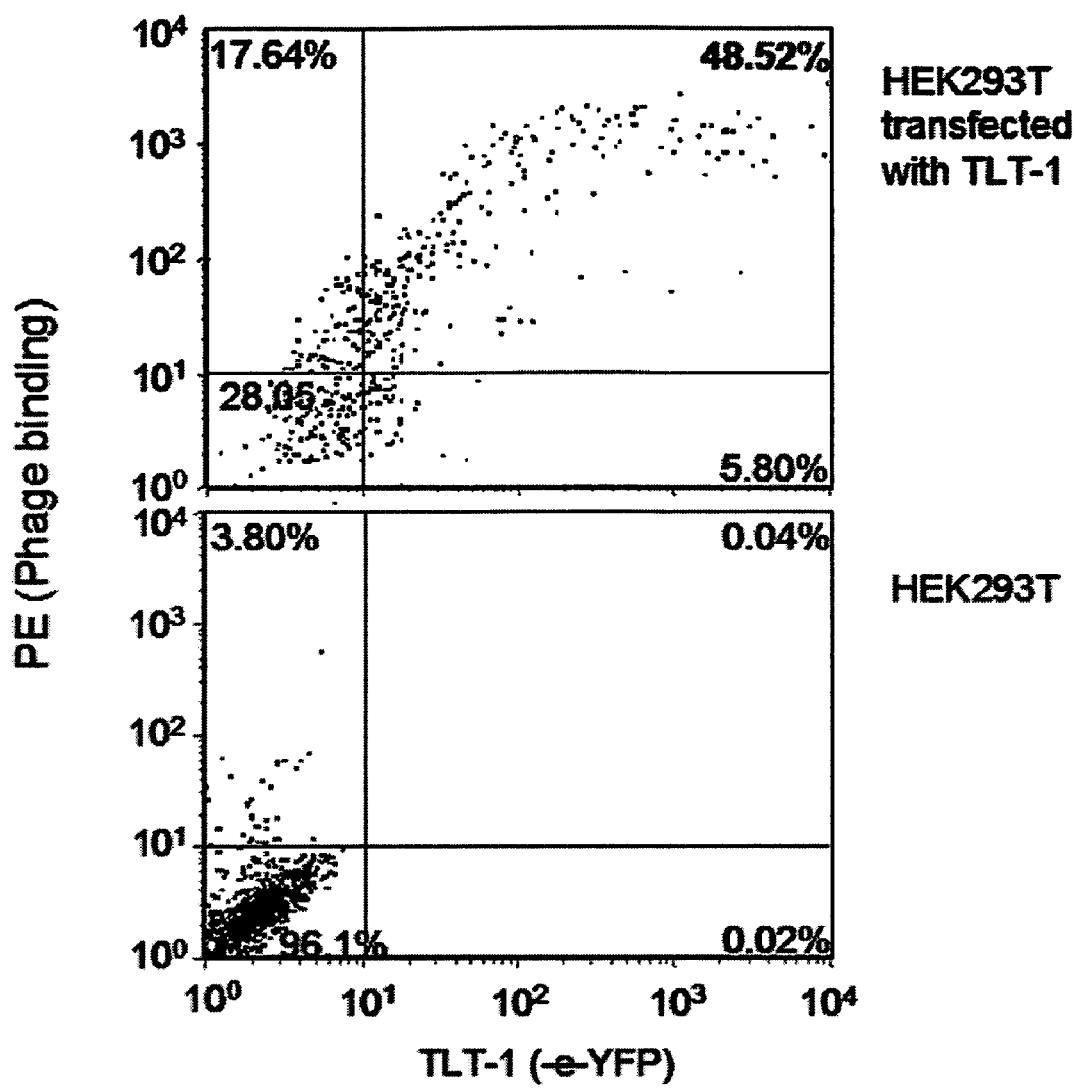
Figure 2 (2/2)

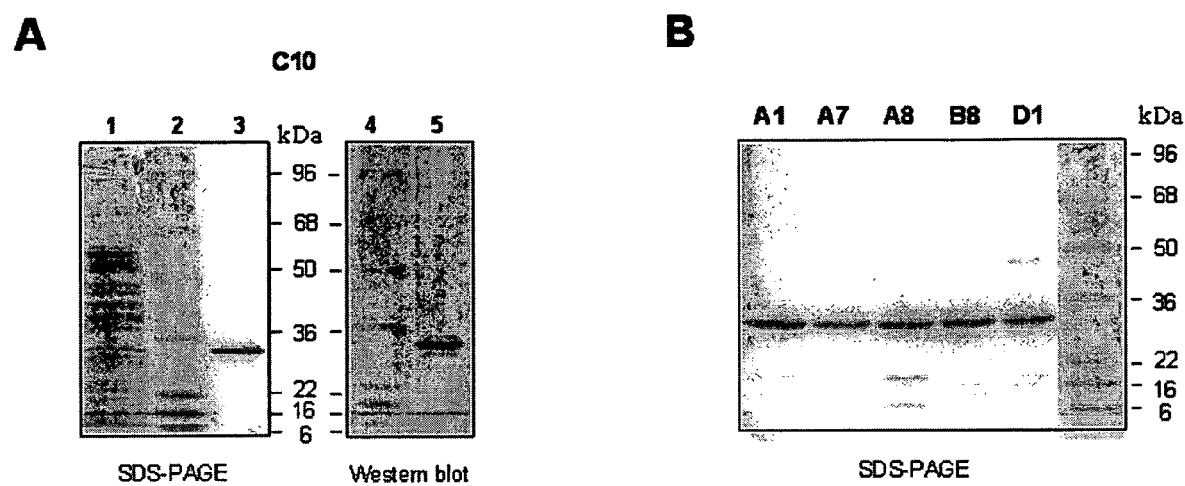
Figure 3 (1/2)

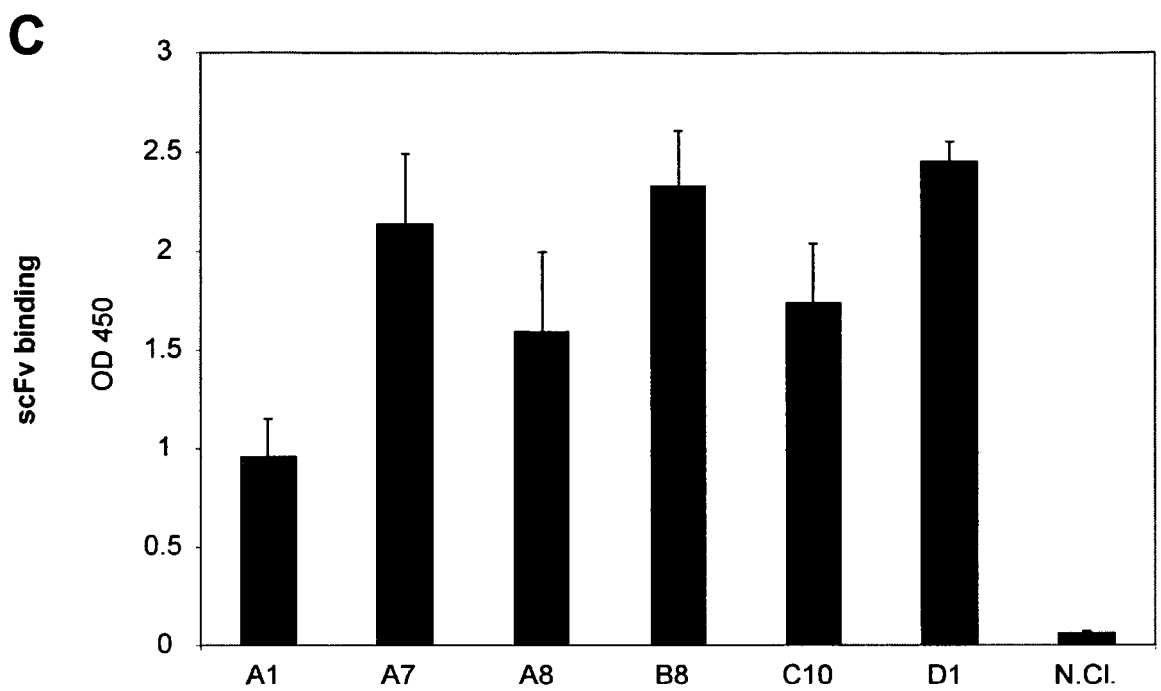
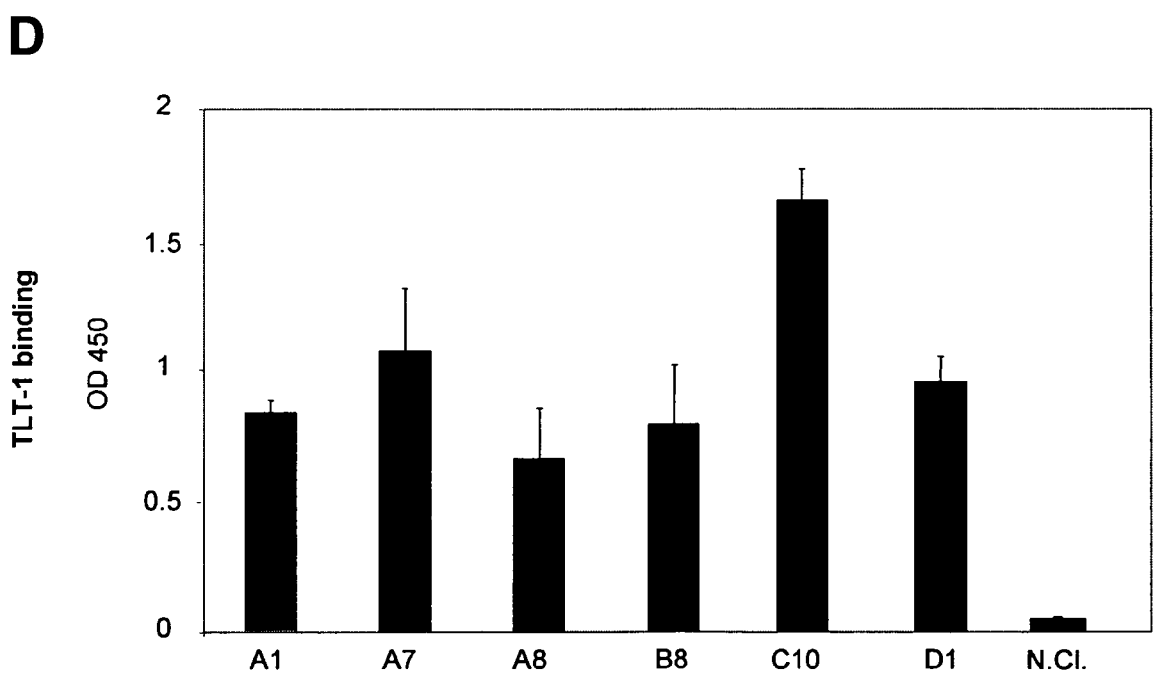
Figure 3 (2/2)

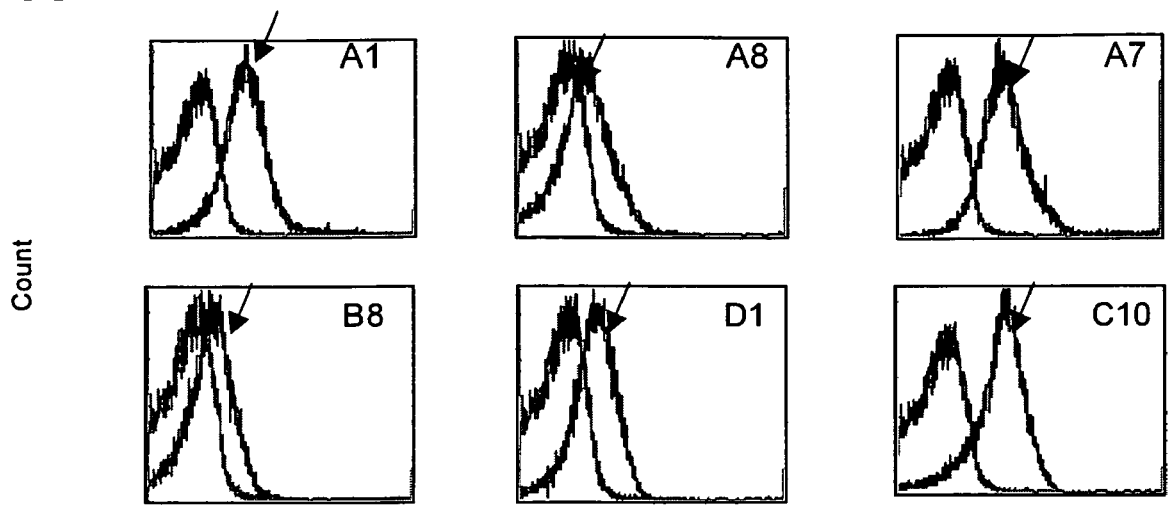
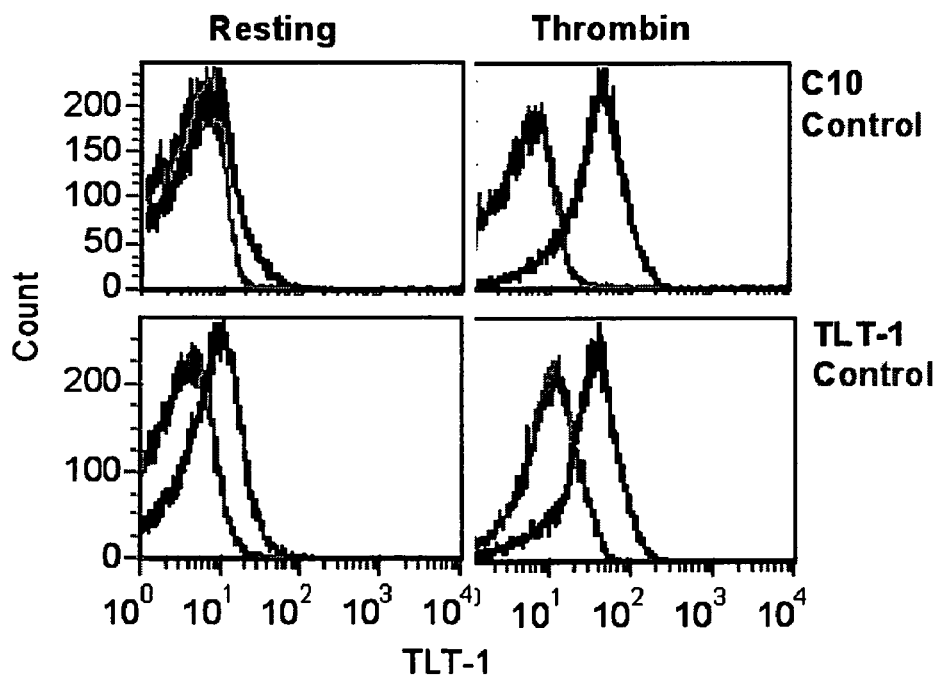
Figure 4 (1/2)

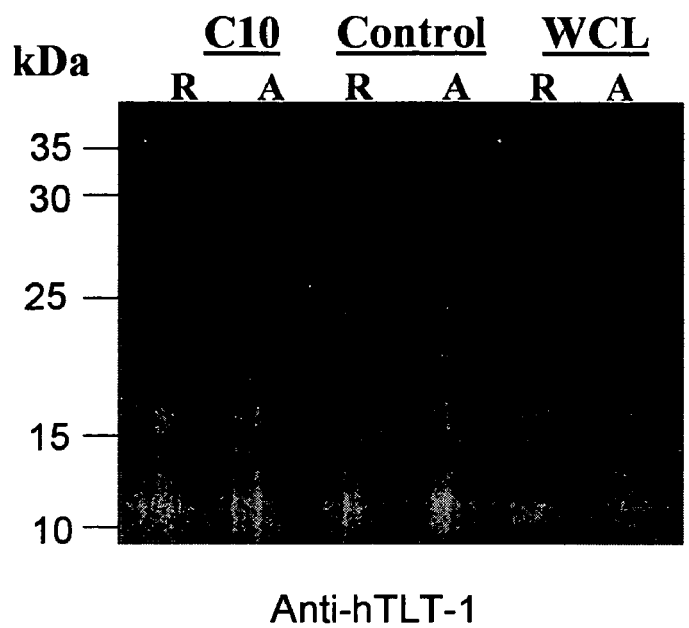
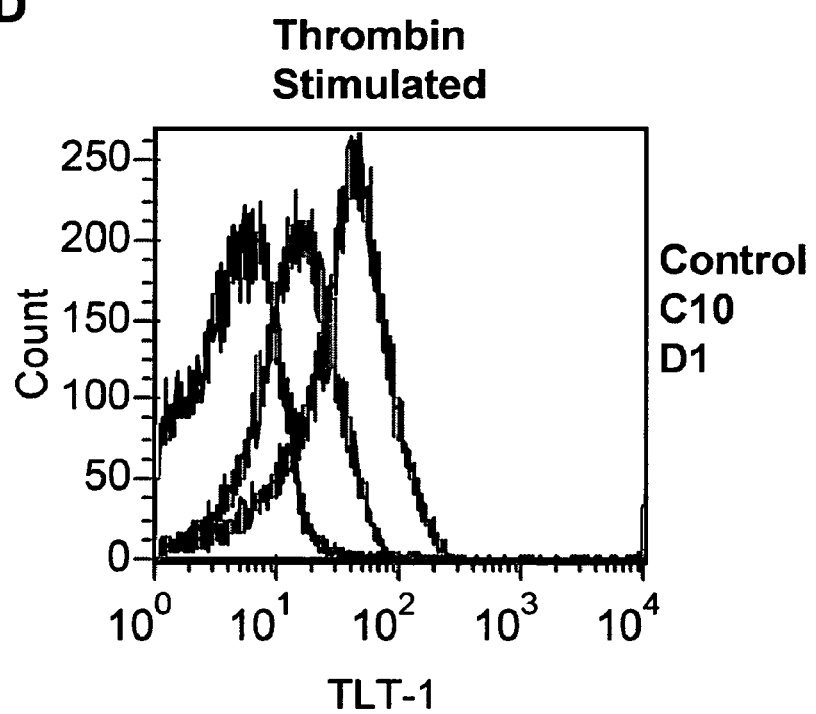
Figure 4 (2/2)

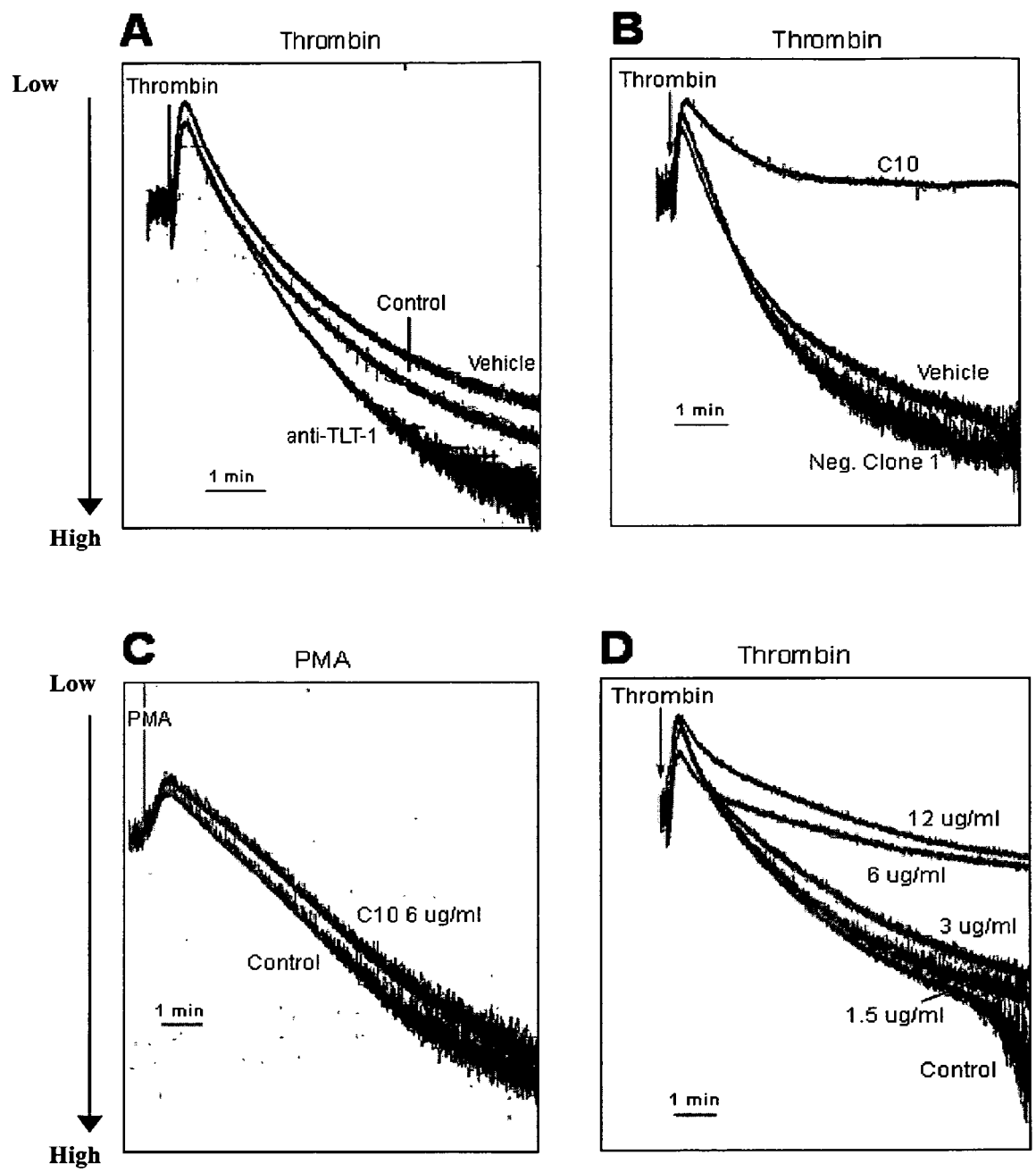
Figure 5 (1/2)

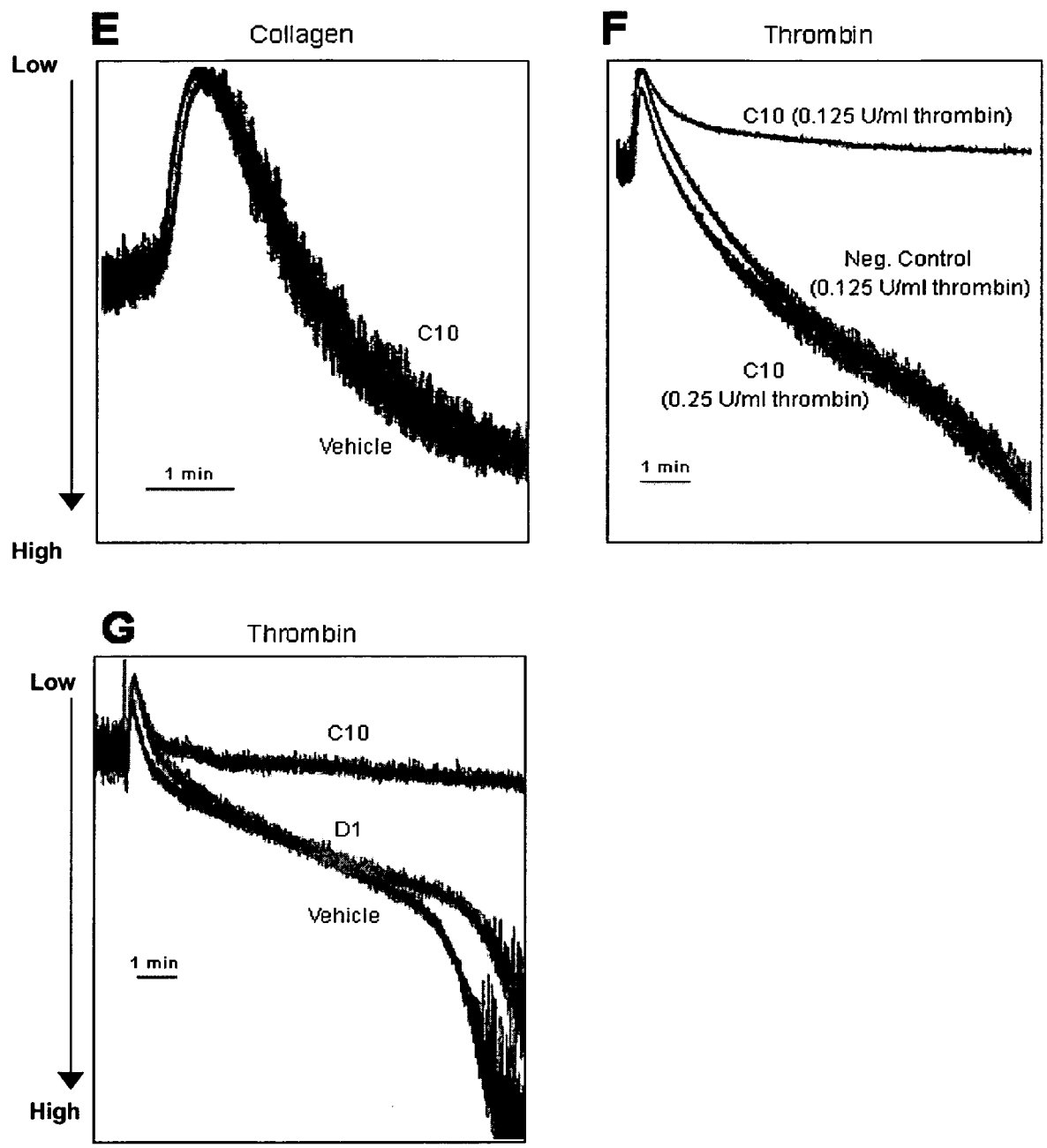
Figure 5 (2/2)

SEQ ID NO: 1

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAGGTATTTCTTCTACTGGTGGTGCTACAACTTACGCA
GACTCCGTGAAGGGCCGGTTCACCATCTCCAGAGACAATTCCAAGAACACGCTGTATCTGCAA
ATGAACAGCCTGAGAGCCGAGGACACGGCCGTATATTACTGTGCGAAATCTACTTATGATTTT
GATTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATGGTGCATCCACTTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGAATGCTGATGCTCCTACTAC
GTTCGGCCAAGGGACCAAGGTGGAAATCAAACGGGCGGCCGCACATCATCATCACCATCACG
GGGCCGCAGAACAAAAACTCATCTCAGAAGAGGATCTGAATGGGGCCGCATAG

SEQ ID NO: 2

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAGGTATTGGTACTACTGGTTATGCTACAGCTTACGCA
GACTCCGTGAAGGGCAGGTTCACCATCTCCAGAGACAATTCCAAGAACACGCTGTATCTGCAA
ATGAACAGCCTGAGAGCCGAGGACACGGCCGTATACTACTGTGCGAAAGGTAATTCTGGTTTT
GACTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATACTGCATCCACCTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGTCTAGTACTGATCCTGGTAC
GTTCGGCCAAGGGACCAAGGTGGAAATCAAACGGGCGGCCGCACATCATCATCACCATCACG
GGGCCGCAGAACAAAAACTCATCTCAGAAGAGGATCTGAATGGGGCCGCATAG

SEQ ID NO: 3

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAGGTATTGGTACTACTGGTTATAGTACAGCTTACGCA
GACTCCGTGAAGGGCCGGTTCACCATCTCCAGAGACAATTCCAAGAACACGCTGTATCTGCAA
ATGAACAGCCTGAGAGCCGAGGACACGGCCGTATATTACTGTGCGAAAACTGCTTATACTTTT
GACTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATTCTGCATCCACTTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGAATAGTACTTATCCTGCTAC
GTTCGGCCAAGGGACCAAGGTGGAAATCAAACGGGCGGCCGCACATCATCATCACCATCACG
GGGCCGCAGAACAAAAACTCATCTCAGAAGAGGATCTGAATGGGGCCGCATAG

Figure 6 (1/2)

SEQ ID NO: 4

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAGCTATTGGTAGTTATGGTTCTGCTACAGCTTACGCA
GACTCCGTGAAGGGCCGGTTCACCATCTCCAGAGACAATTCCAAGAACACGCTGTATCTGCAA
ATGAACAGCCTGAGAGCCGAGGACACGGCCGTATATTACTGTGCGAAAAATGGTTATGATTTT
GACTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATAATGCATCCGGTTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGTCTGCTGCTAATCCTTCTACG
TTCGGCCAAGGGACCAAGGTGGAAATCAAACGGGCGGCCGCACATCATCATCACCATCACGG
GGCCGCAGAACAAAAACTCATCTCAGAAGAGGATCTGAATGGGGCCGCATAG

SEQ ID NO: 5

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAAATATTACTGCTAGTGGTTATGCTACAGCTTACGCA
GACTCCGTGAAGGGCCGGTTCACCATCTCCAGAGACAATTCCAAGAACACGCTGTATCTGCAA
ATGAACAGCCTGAGAGCCGAGGACACGGCCGTATATTACTGTGCGAAAACTACTGCTACTTTT
GACTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATGATGCATCCAATTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGGATACTGCTTCTCCTTCTACG
TTCGGCCAAGGGACCAAGGTGGAAATCAAACGGGCGGCCGCACATCATCATCACCATCACGG
GGCCGCAGAACAAAAACTCATCTCAGAAGAGGATCTGAATGGGGCCGCATAG

SEQ ID NO: 6

ATGGCCGAGGTGCAGCTGTTGGAGTCTGGGGGAGGCTTGGTACAGCCTGGGGGGTCCCTGAG
ACTCTCCTGTGCAGCCTCTGGATTCACCTTTAGCAGCTATGCCATGAGCTGGGTCCGCCAGGCT
CCAGGGAAGGGGCTGGAGTGGGTCTCAGCTATTGGTACTACTGGTTATGCTACAGCTTACGCA
GACTCCGTGAAGGGCCGGTTCACCATCTCCAGAGACAATTCCAAGAACACGCTGTATCTGCAA
ATGAACAGCCTGAGAGCCGAGGACACGGCCGTATATTACTGTGCGAAAGCTAATTCTTATTTT
GACTACTGGGGCCAGGGAACCCTGGTCACCGTCTCGAGCGGTGGAGGCGGTTCAGGCGGAGG
TGGCAGCGGCGGTGGCGGGTCGACGGACATCCAGATGACCCAGTCTCCATCCTCCCTGTCTGC
ATCTGTAGGAGACAGAGTCACCATCACTTGCCGGGCAAGTCAGAGCATTAGCAGCTATTTAAA
TTGGTATCAGCAGAAACCAGGGAAAGCCCCTAAGCTCCTGATCTATAGTGCATCCACTTTGCA
AAGTGGGGTCCCATCAAGGTTCAGTGGCAGTGGATCTGGGACAGATTTCACTCTCACCATCAG
CAGTCTGCAACCTGAAGATTTTGCAACTTACTACTGTCAACAGGATTCTACTTCTCCTGATACG
TTCGGCCAAGGGACCAAGGTGGAAATCAAACGGGCGGCCGCACATCATCATCACCATCACGG
GGCCGCAGAACAAAAACTCATCTCAGAAGAGGATCTGAATGGGGCCGCATAG

```
                        SEQUENCE LISTING

<160> NUMBER OF SEQ ID NOS: 37

<210> SEQ ID NO 1
<211> LENGTH: 807
<212> TYPE: DNA
<213> ORGANISM: Homo sapiens

<400> SEQUENCE: 1
atggccgagg tgcagctgtt ggagtctggg ggaggcttgg tacagcctgg ggggtccctg      60
agactctcct gtgcagcctc tggattcacc tttagcagct atgccatgag ctgggtccgc     120
caggctccag ggaaggggct ggagtgggtc tcaggtattt cttctactgg tggtgctaca     180
acttacgcag actccgtgaa gggccggttc accatctcca gagacaattc caagaacacg     240
ctgtatctgc aaatgaacag cctgagagcc gaggacacgg ccgtatatta ctgtgcgaaa     300
tctacttatg attttgatta ctggggccag ggaaccctgg tcaccgtctc gagcggtgga     360
ggcggttcag gcggaggtgg cagcggcggt ggcggtcga cggacatcca gatgacccag     420
tctccatcct ccctgtctgc atctgtagga gacagagtca ccatcacttg ccgggcaagt     480
cagagcatta gcagctattt aaattggtat cagcagaaac cagggaaagc ccctaagctc     540
ctgatctatg gtgcatccac tttgcaaagt ggggtcccat caaggttcag tggcagtgga     600
tctgggacag atttcactct caccatcagc agtctgcaac tgaagatttt gcaacttac     660 tactgtcaac agaatgctga tgctcctact acgttcggcc aagggaccaa ggtggaaatc     720
aaacgggcgg ccgcacatca tcatcaccat cacggggccg cagaacaaaa actcatctca     780
gaagaggatc tgaatggggc cgcatag                                          807

<210> SEQ ID NO 2
<211> LENGTH: 807
<212> TYPE: DNA
<213> ORGANISM: Homo sapiens

<400> SEQUENCE: 2
```

```
atggccgagg tgcagctgtt ggagtctggg ggaggcttgg tacagcctgg ggggtccctg    60
agactctcct gtgcagcctc tggattcacc tttagcagct atgccatgag ctgggtccgc   120
caggctccag ggaaggggct ggagtgggtc tcaggtattg gtactactgg ttatgctaca   180
gcttacgcag actccgtgaa gggcaggttc accatctcca gagacaattc caagaacacg   240
ctgtatctgc aaatgaacag cctgagagcc gaggacacgg ccgtatacta ctgtgcgaaa   300
ggtaattctg gttttgacta ctggggccag ggaaccctgg tcaccgtctc gagcggtgga   360
ggcggttcag gcggaggtgg cagcggcggt ggcgggtcga cggacatcca gatgacccag   420
tctccatcct ccctgtctgc atctgtagga gacagagtca ccatcacttg ccgggcaagt   480
cagagcatta gcagctattt aaattggtat cagcagaaac cagggaaagc ccctaagctc   540
ctgatctata ctgcatccac cttgcaaagt ggggtcccat caaggttcag tggcagtgga   600
tctgggacag atttcactct caccatcagc agtctgcaac tgaagatttt gcaacttac    660 tactgtcaac agtctagtac tgatcctggt acgttcggcc aagggaccaa ggtggaaatc   720
aaacgggcgg ccgcacatca tcatcaccat cacggggccg cagaacaaaa actcatctca   780
gaagaggatc tgaatggggc cgcatag                                       807

<210> SEQ ID NO 3
<211> LENGTH: 807
<212> TYPE: DNA
<213> ORGANISM: Homo sapiens

<400> SEQUENCE: 3
atggccgagg tgcagctgtt ggagtctggg ggaggcttgg tacagcctgg ggggtccctg    60
agactctcct gtgcagcctc tggattcacc tttagcagct atgccatgag ctgggtccgc   120
caggctccag ggaaggggct ggagtgggtc tcaggtattg gtactactgg ttatagtaca   180
gcttacgcag actccgtgaa gggccggttc accatctcca gagacaattc caagaacacg   240
ctgtatctgc aaatgaacag cctgagagcc gaggacacgg ccgtatatta ctgtgcgaaa   300
actgcttata cttttgacta ctggggccag ggaaccctgg tcaccgtctc gagcggtgga   360
ggcggttcag gcggaggtgg cagcggcggt ggcgggtcga cggacatcca gatgacccag   420
tctccatcct ccctgtctgc atctgtagga gacagagtca ccatcacttg ccgggcaagt   480
cagagcatta gcagctattt aaattggtat cagcagaaac cagggaaagc ccctaagctc   540
ctgatctatt ctgcatccac tttgcaaagt ggggtcccat caaggttcag tggcagtgga   600
tctgggacag atttcactct caccatcagc agtctgcaac tgaagatttt gcaacttac    660 tactgtcaac agaatagtac ttatcctgct acgttcggcc aagggaccaa ggtggaaatc   720
aaacgggcgg ccgcacatca tcatcaccat cacggggccg cagaacaaaa actcatctca   780
gaagaggatc tgaatggggc cgcatag                                       807

<210> SEQ ID NO 4
<211> LENGTH: 807
<212> TYPE: DNA
<213> ORGANISM: Homo sapiens

<400> SEQUENCE: 4
atggccgagg tgcagctgtt ggagtctggg ggaggcttgg tacagcctgg ggggtccctg    60
agactctcct gtgcagcctc tggattcacc tttagcagct atgccatgag ctgggtccgc   120
caggctccag ggaaggggct ggagtgggtc tcagctattg gtagttatgg ttctgctaca   180
gcttacgcag actccgtgaa gggccggttc accatctcca gagacaattc caagaacacg   240
```

```
ctgtatctgc aaatgaacag cctgagagcc gaggacacgg ccgtatatta ctgtgcgaaa    300
aatggttatg attttgacta ctggggccag ggaaccctgg tcaccgtctc gagcggtgga    360
ggcggttcag gcggaggtgg cagcggcggt ggcgggtcga cggacatcca gatgacccag    420
tctccatcct ccctgtctgc atctgtagga gacagagtca ccatcacttg ccgggcaagt    480
cagagcatta gcagctattt aaattggtat cagcagaaac cagggaaagc ccctaagctc    540
ctgatctata atgcatccgg tttgcaaagt ggggtcccat caaggttcag tggcagtgga    600
tctgggacag atttcactct caccatcagc agtctgcaac tgaagatttt gcaacttac     660 tactgtcaac agtctgctgc taatccttct acgttcggcc aagggaccaa ggtggaaatc    720
aaacgggcgg ccgcacatca tcatcaccat cacggggccg cagaacaaaa actcatctca    780
gaagaggatc tgaatggggc cgcatag                                        807
```

<210> SEQ ID NO 5
<211> LENGTH: 807
<212> TYPE: DNA
<213> ORGANISM: Homo sapiens

<400> SEQUENCE: 5

```
atggccgagg tgcagctgtt ggagtctggg ggaggcttgg tacagcctgg ggggtccctg     60
agactctcct gtgcagcctc tggattcacc tttagcagct atgccatgag ctgggtccgc    120
caggctccag ggaaggggct ggagtgggtc tcaaatatta ctgctagtgg ttatgctaca    180
gcttacgcag actccgtgaa gggccggttc accatctcca gagacaattc caagaacacg    240
ctgtatctgc aaatgaacag cctgagagcc gaggacacgg ccgtatatta ctgtgcgaaa    300
actactgcta cttttgacta ctggggccag ggaaccctgg tcaccgtctc gagcggtgga    360
ggcggttcag gcggaggtgg cagcggcggt ggcgggtcga cggacatcca gatgacccag    420
tctccatcct ccctgtctgc atctgtagga gacagagtca ccatcacttg ccgggcaagt    480
cagagcatta gcagctattt aaattggtat cagcagaaac cagggaaagc ccctaagctc    540
ctgatctatg atgcatccaa tttgcaaagt ggggtcccat caaggttcag tggcagtgga    600
tctgggacag atttcactct caccatcagc agtctgcaac tgaagatttt gcaacttac     660 tactgtcaac aggatactgc ttctccttct acgttcggcc aagggaccaa ggtggaaatc    720
aaacgggcgg ccgcacatca tcatcaccat cacggggccg cagaacaaaa actcatctca    780
gaagaggatc tgaatggggc cgcatag                                        807
```

<210> SEQ ID NO 6
<211> LENGTH: 807
<212> TYPE: DNA
<213> ORGANISM: Homo sapiens

<400> SEQUENCE: 6

```
atggccgagg tgcagctgtt ggagtctggg ggaggcttgg tacagcctgg ggggtccctg     60
agactctcct gtgcagcctc tggattcacc tttagcagct atgccatgag ctgggtccgc    120
caggctccag ggaaggggct ggagtgggtc tcagctattg gtactactgg ttatgctaca    180
gcttacgcag actccgtgaa gggccggttc accatctcca gagacaattc caagaacacg    240
ctgtatctgc aaatgaacag cctgagagcc gaggacacgg ccgtatatta ctgtgcgaaa    300
gctaattctt attttgacta ctggggccag ggaaccctgg tcaccgtctc gagcggtgga    360
ggcggttcag gcggaggtgg cagcggcggt ggcgggtcga cggacatcca gatgacccag    420
```

-continued

```
tctccatcct ccctgtctgc atctgtagga gacagagtca ccatcacttg ccgggcaagt        480
cagagcatta gcagctattt aaattggtat cagcagaaac cagggaaagc ccctaagctc        540
ctgatctata gtgcatccac tttgcaaagt ggggtcccat caaggttcag tggcagtgga        600
tctgggacag atttcactct caccatcagc agtctgcaac tgaagatttt gcaacttac         660 tactgtcaac aggattctac ttctcctgat acgttcggcc aagggaccaa ggtggaaatc        720
aaacgggcgg ccgcacatca tcatcaccat cacggggccg cagaacaaaa actcatctca        780
gaagaggatc tgaatggggc cgcatag                                             807
```

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
caggaaacag ctatgac                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ctatgcggcc ccattca                17

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cgacccgcca ccgccgctg              19

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

His His His His His His His His His His
 1               5                  10

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atgggcctca ccctgctctt g           21

```
<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctggatgga gtctgattg                                                    19

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ile Gly Thr Thr Gly Tyr Ala Thr Ala Tyr Ala Asp Ser Val Lys
 1               5                  10                  15
Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ile Gly Ser Tyr Gly Ser Ala Thr Ala Tyr Ala Asp Ser Val Lys
 1               5                  10                  15
Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ile Gly Thr Thr Gly Tyr Ser Thr Ala Tyr Ala Asp Ser Val Lys
 1               5                  10                  15
Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ile Thr Ala Ser Gly Tyr Ala Thr Ala Tyr Ala Asp Ser Val Lys
 1               5                  10                  15
Gly
```

```
<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ile Ser Ser Thr Gly Gly Ala Thr Thr Tyr Ala Asp Ser Val Lys
 1               5                  10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ile Gly Thr Thr Gly Tyr Ala Thr Ala Tyr Ala Asp Ser Val Lys
 1               5                  10                  15

Gly

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Asn Ser Gly Phe Asp Tyr
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Gly Tyr Asp Phe Asp Tyr
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ala Tyr Thr Phe Asp Tyr
 1               5

<210> SEQ ID NO 22
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 22

Thr Thr Ala Thr Phe Asp Tyr
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Thr Tyr Asp Phe Asp Tyr
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Asn Ser Tyr Phe Asp Tyr
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ala Ser Thr Leu Gln Ser
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Ala Ser Gly Leu Gln Ser
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ala Ser Thr Leu Gln Ser
  1               5

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ala Ser Asn Leu Gln Ser
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Ser Thr Leu Gln Ser
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ala Ser Thr Leu Gln Ser
 1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Ser Ser Thr Asp Pro Gly Thr
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Ser Ala Ala Asn Pro Ser Thr
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Gln Gln Asn Ser Thr Tyr Pro Ala Thr
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Asp Thr Ala Ser Pro Ser Thr
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Asn Ala Asp Ala Pro Thr Thr
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Asp Ser Thr Ser Pro Asp Thr
 1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser Gly Gly Gly Gly Ser
 1               5                  10                  15
```

ANTI-TREM-LIKE TRANSCRIPT-1 (TLT-1) ANTIBODIES AND COMPOSITIONS

STATEMENT OF RIGHTS TO INVENTIONS MADE UNDER FEDERALLY SPONSORED RESEARCH

This invention was funded, in part by the Intramural Research Program of the NIH, National Cancer Institute, Center for Cancer Research, and by Grant Number 2G12RR3035 from the National Center for Research Resources (NCRR), a Component of the NIH, at least in part, by the intramural research program of the NIH NCI, CCR. Accordingly, the U.S. Government may have certain rights to this invention.

CROSS-REFERENCE TO RELATED APPLICATIONS/PATENTS & INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

The present invention relates to methods and compositions for modulating platelet aggregation, and methods and compositions for treating a disease or disorder associated with platelet aggregation in a subject, comprising administering a single chain TREM-like transcript-1 (TLT-1) antibody, or a functional fragment or variant thereof, in an amount effective to modulate platelet aggregation.

The triggering receptors expressed on myeloid cells (TREMs) are an emerging family of activating receptors expressed on various cells of the myeloid lineage (Bouchon, A. et al. (2000) J. Immunol. 164:4991-4995; Bouchon, A. et al. (2001) J. Exp. Med. 194:1111-1122; Daws, M. R. et al. (2001) Eur. J. Immunol. 31:783-791; Chung, D. H. et al. (2002) Eur. J. Immunol. 32:59-66). The TREMs represent a loose cluster (150 kb) on mouse chromosome 17, and the cluster's genomic organization is highly conserved on human chromosome 6. Although the family members possess only 30% amino acid identity, each member consists of a leader sequence, single V-set Ig domain, short cytoplasmic tail, and transmembrane domain containing a positively charged residue, suggesting interaction with a signaling polypeptide (Daws, M. R. et al. (2001) Eur. J. Immunol. 31:783-791; Chung, D. H. et al. (2002) Eur. J. Immunol. 32:59-66). Biochemical analysis has demonstrated that of the four TREM sequences described to date, TREMs 1, 2, and 3 associate with the activating signaling chain DAP 12, and TREM-4 is predicted to as well (Bouchon, A. et al. (2000) J. Immunol. 164:4991-4995; Bouchon, A. et al. (2001) J. Exp. Med. 194: 1111-1122; Daws, M. R. et al. (2001) Eur. J. Immunol. 31:783-791; Chung, D. H. et al. (2002) Eur. J. Immunol. 32:59-66; Bouchon, A. et al. (2001) Nature 410:1103-1107). Bouchon et al. uncovered the importance of this family in the regulation of multiple facets of the immune response (Bouchon, A. et al. (2000) J. Immunol. 164:4991-4995; Bouchon, A. et al. (2001) J. Exp. Med. 194:1111-1122; Bouchon, A. et al. (2001) Nature 410:1103-1107). These studies defined TREM11 as an important mediator of septic shock (Bouchon, A. et al. (2000) J. Immunol. 164:4991-4995; Bouchon, A. et al. (2001) Nature 410:1103-1107; Nathan, C. and Ding, A. (2001) Nat. Med. 7:530-532; Cohen, J. (2001) Lancet 358: 776-778), and TREM-2 as playing a unique role in dendritic cell maturation and, therefore, T-cell priming (Bouchon, A. et al. (2001) J. Exp. Med. 194:1111-1122; Bachmann, M. F. (2002) Trends Immunol. 23:10).

Platelets, also referred to as "blood platelets" or "peripheral blood platelets," are small cells that lack a nucleus, but have a highly organized cytoskeleton, unique cell-surface receptors, and specialized secretory granules. Human blood contains nearly a trillion platelets, which respond to blood vessel injury by changing shape, secreting granule contents, and aggregation (Italiano, J. E., Jr. et al. (1999) J. Cell Biol. 147:1299-1312). These responses cause blood clotting to aid repair of injury and stop bleeding, but can also cause unwanted clots that lead to tissue ischemia and/or infarction, including stroke and heart attack. Platelets are produced through the terminal differentiation of megakaryocytes. Each mature megakaryocyte produces and releases hundreds of platelets into circulation (Kaufinan et al. (1965) Blood 26:720-728; Harker and Finch (1969) J. Clin. Invest. 48:963-974; and Trowbridge et al. (1984) Clin. Phys. Physiol. Meas. 5:145-156). Megakaryocytes, which make up about <0.1% of all cells in the bone marrow (Italiano et al. (1999) supra), are polyploid cells whose size and DNA content correlate directly with the circulating platelet mass (Ebbe and Stohlman (1965) Blood 26:20-34). Mature megakaryocytes assemble a unique set of organelles, including alpha granules, dense bodies, and an extensive system of internal membranes (Shivdasani, R. A. (2001) Stem Cells 19:397-407). Differentiated megakaryocytes extrude long cytoplasmic processes ("proplatelets") that serve as the immediate precursors of circulating platelets (Choi, E. S. et al. (1995) Blood 85:402-413; Cramer, E. M. et al. (1997) Blood 89:2336-2346; Norol, F. et al. (1998) Blood 91:830-843). Megakaryocyte and platelet differentiation is controlled by a number of transcription factors, including GATA-1, FOG-1, and NF-E2 (Shivdasani et al. (2001) supra), as well as factors such as thrombopoietin.

Platelets play a crucial role in the mortality associated with cardiovascular disease (CVD) and therefore are a primary target for therapeutic intervention. Platelets are believed to assist in the advancement of CVD (Ruggeri Z M. Nat Med 2002; 8: 1227-34.), and it is estimated that 50-60% of sudden coronary death cases are caused by ruptured plaques consisting largely of platelets and fibrin (Burke A P, et al. N Engl J Med 1997; 336: 1276-82; Virmani R, et al. Arterioscler Thromb Vasc Biol 2000; 20: 1262-75). Errant platelet-mediated thrombosis is a common and life-threatening disease in the United State and through-out the world, and carries with it high mortality rates. To improve patient outcomes, drugs targeting platelet agonists are commonly used. Current efforts in anti-platelet therapy focus on separating the haemostatic function of platelets from their thrombotic nature (Phillips D R, et al. J Thromb Haemost 2005; 3: 1577-89; Nieswandt B, Aktas B, Moers A, Sachs U J. Platelets in atherothrombosis: lessons from mouse models. J Thromb Haemost 2005; 3: 1725-36). The new generation of antiplatelet therapies target specific activation pathways. Examples are clopidogrel, which inhibits platelet activation through the irreversible inhibition of the P2Y12 receptor (A randomised, blinded, trial of clopidogrel versus aspirin in patients at risk of ischaemic events (CAPRIE) CAPRIE Steering Committee. Lancet 1996; 348: 1329-39) and abciximab, a monoclonal F(ab')2 fragment that target the platelet glycoprotein (GP) IIb/IIIa (Popma J J, et al. J Invasive Cardiol 1994; 6 Suppl A: 19A-28A; Genetta T B, et al. Ann Pharmacother 1996; 30: 251-7.). Although these therapies have shown partial efficacy and side effects, they demonstrate the utility of platelet membrane receptors as a new class of therapeutic targets for the regulation of platelet functions.

Thus, intervention with TLT-1 may have significant impact on managing and treating a range of diseases. Given the importance of platelets in blood clotting and wound healing, as well as their involvement in many disorders such as stroke and heart disease, and in sepsis and septic shock, there exists a need in the art for agents and methods that can modulate platelet aggregation and/or function.

Citation or identification of any document in this application is not an admission that such document is available as prior art to the present invention.

SUMMARY OF THE INVENTION

The present invention relates to methods and compositions for modulating platelet activity, and methods and compositions for treating a disease or disorder associated with platelet activity in a subject, comprising administering a single chain anti-TREM-like transcript-1 (TLT-1) antibody or a functional fragment or variant thereof in an amount effective to modulate platelet activity.

A platelet activity as used herein includes an activity which involves the action of platelets, including, but not limited to, platelet aggregation, adhesion to the site of a wound, activation (e.g., release of blood clotting factors), induction of blood clotting (e.g., induction of fibrin formation), inhibition of bleeding, and induction of wound healing.

Platelet mediated activity may be regulated by factors that are secreted by the platelets, including platelet-derived growth factor, platelet factor 4, RANTES, thrombospondin, transforming growth factor-beta, nitric oxide, and CD-40 ligand.

In preferred embodiments, the invention relates to methods and compositions for modulating platelet aggregation, and methods and compositions for treating a disease or disorder associated with platelet aggregation in a subject, comprising administering a single chain anti-TREM-like transcript-1 (TLT-1) antibody or a functional fragment or variant thereof in an amount effective to modulate platelet aggregation.

In one aspect, the invention features a method of modulating platelet activity in a subject, the method comprising administering to the subject an effective amount of a single chain anti-TLT-1 antibody or a function fragment thereof, thereby modulating platelet activity.

In another aspect, the invention features a method of modulating platelet aggregation in a subject, the method comprising administering to the subject a single chain anti-TLT-1 antibody or a functional fragment thereof in an amount effective to modulate platelet aggregation, thereby modulating platelet aggregation.

In another aspect, the invention features a method of treating a disease or disorder associated with platelet aggregation in a subject, the method comprising administering to the subject a single chain anti-TLT-1 antibody or a functional fragment thereof in an amount effective to modulate platelet aggregation, thereby treating a disease or disorder associated with platelet aggregation.

In another particular aspect, the invention features a method of modulating platelet aggregation in a subject at risk for a disease or disorder associated with platelet aggregation, the method comprising administering to the subject a single chain anti-TLT-1 antibody or a functional fragment thereof in an amount effective to modulate platelet aggregation, thereby modulating platelet aggregation in the subject.

In a related aspect, the invention features a method of treating a subject at risk for a disease or disorder associated with platelet aggregation, the method comprising administering to the subject a single chain anti-TLT-1 antibody or a functional fragment or variant thereof in an amount effective to modulating platelet aggregation, thereby treating the subject.

In another aspect, the invention features a method of treating a subject at risk for a disease or disorder associated with platelet aggregation, the method comprising administering to the subject a single chain anti-TLT-1 antibody or a functional fragment or variant thereof in an amount effective to modulating platelet aggregation, thereby treating the subject.

In yet another aspect, the invention features a method of treating a subject that has currently or previously been treated for a disease or disorder associated with platelet aggregation, the method comprising administering to the subject a single chain anti-TLT-1 antibody or a functional fragment or variant thereof in an amount effective to modulate platelet aggregation, thereby treating the subject.

In one embodiment of any of the above-described aspects, the modulation is an inhibition of platelet aggregation. In another embodiment, the modulation is measured by a method selected from platelet aggregation test, aggregrometry assay and microtiter plate assay. In another embodiment, the sample is from a mammal. In a particular embodiment, the sample is selected from independent platelets or whole blood. In another particular embodiment, platelet aggregation is mediated by thrombin.

In another embodiment of any of the above-described aspects, the disease or disorder associated with platelet aggregation is selected from cardiovascular diseases, inflammatory diseases, cancer, and sepsis. In a related embodiment, the cardiovascular disease is selected from the group consisting of: thrombosis, heart attack, atherosclerosis, and stroke.

In a further embodiment of any of the above-described aspects, the method is performed in combination with one or more additional therapies. In a related embodiment of any of the above-described aspects, the one or more additional therapies is selected from chemotherapy, antibiotic therapy, surgery, anticoagulant therapies, and anti-inflammatory therapies. In a further embodiment, the therapy is either therapeutic or prophylactic.

In another aspect, the invention features a method of diagnosing a subject with a disease or disorder associated with platelet aggregation, the method comprising detecting in the subject a soluble fragment of TLT-1 receptor, or a functional fragment or variant thereof, and thereby diagnosing the subject with a disease or disorder associated with platelet aggregation.

In a related aspect, the invention features a method of diagnosing a subject at risk for a disease or disorder associated with platelet aggregation, the method comprising detecting in the subject a soluble fragment of TLT-1 receptor, or a functional fragment or variant thereof, thereby diagnosing the subject at risk for a disease or disorder associated with platelet aggregation.

In any of the above aspects, a decreased level of expression relative to the level of expression in a reference indicates that the subject has or has a propensity to develop a disease or disorder associated with platelet aggregation.

In another aspect, the invention features a method of diagnosing a subject as having, or having a propensity to develop, a disease or disorder associated with platelet aggregation, the method comprising determining the level of a soluble fragment of TLT-1 receptor in a subject, wherein a decreased level of expression relative to the level of expression in a reference, indicates that the subject has or has a propensity to develop a disease or disorder associated with platelet aggregation.

In one embodiment, the level of soluble fragment of TLT-1 receptor is determined using a single chain TLT-1 antibody, or a functional fragment thereof, in an immunological assay. In another embodiment, the reference is a control subject sample. In a further embodiment, the subject is a human.

In one embodiment of any of the above aspects, the single chain anti-TLT-1 antibody comprises a functional fragment thereof that binds to TLT-1. In another embodiment of any of the above aspects, the single chain TLT-1 antibody or a functional fragment thereof has specificity to the extracellular domain of TLT-1. In yet another embodiment of any of the above aspects, the single chain TLT-1 antibody or a functional fragment thereof is a monoclonal antibody. In still another embodiment of any of the above aspects, the single chain TLT-1 antibody or a functional fragment thereof is selected from the group consisting of: SEQ ID NO: 1, SEQ ID NO: 2 or SEQ ID NO: 3. In another embodiment of any of the above aspects, the single chain TLT-1 antibody or a functional fragment thereof is a sequence comprising any one of SEQ ID NO: 1, SEQ ID NO: 2 or SEQ ID NO: 3.

In one embodiment of any of the above aspects, the single chain anti-TLT-1 antibody comprises a functional fragment or variant thereof that binds to TLT-1. In another embodiment of any of the above aspects, the single chain anti-TLT-1 antibody or a functional fragment or variant thereof has specificity to the extracellular domain of TLT-1.

In yet another embodiment of any of the above aspects, the single chain anti-TLT-1 antibody or a functional fragment or variant thereof is a full-length antibody.

In another embodiment of any of the above aspects, the single chain anti-TLT-1 antibody or a functional fragment or variant thereof is a monoclonal antibody.

In another embodiment of any of the above aspects, the single chain anti-TLT-1 antibody or a functional fragment or variant thereof is SEQ ID NO: 1. In another embodiment of any of the above aspects, the single chain TLT-1 antibody or a functional fragment or variant thereof is SEQ ID NO: 2. In another embodiment of any of the above aspects, the single chain anti-TLT-1 antibody or a functional fragment or variant thereof is SEQ ID NO: 3.

In another embodiment of any of the above aspects, the single chain anti-TLT-1 antibody or a functional fragment or variant thereof comprises SEQ ID NO: 1. In another embodiment of any of the above aspects, the single chain anti-TLT-1 antibody or a functional fragment or variant thereof comprises SEQ ID NO: 2. In another embodiment of any of the above aspects, the single chain TLT-1 antibody or a functional fragment or variant thereof comprises SEQ ID NO: 3.

In a further embodiment of any of the above aspects, the single chain anti-TLT-1 antibody or a functional fragment or variant thereof is administered by the method selected from the group consisting of: subcutaneous, intramuscular, intraperitoneal, intradermal, oral, intranasal, and aerosol, intravenous, intraarterial.

In one aspect, the invention features a pharmaceutical composition comprising a single chain anti-TLT-1 antibody or a functional fragment or variant thereof that binds to TLT-1.

In another aspect, the invention features a pharmaceutical composition comprising a single chain anti-TLT-1 antibody or a functional fragment or variant thereof has specificity for the extracellular domain of TLT-1.

In a further aspect, the invention features a pharmaceutical composition comprising a single chain anti-TLT-1 antibody or a functional fragment or variant thereof that is a full-length antibody.

In one embodiment of any of the above compositions, the single chain anti-TLT-1 antibody or a functional fragment or variant thereof is designated SEQ ID NO: 1. In another embodiment of any of the above compositions, the single chain anti-TLT-1 antibody or a functional fragment or variant thereof is designated SEQ ID NO: 2. In another embodiment of any of the above compositions, the single chain anti-TLT-1 antibody or a functional fragment or variant thereof is designated SEQ ID NO: 3. In another embodiment of any of the above compositions, the single chain anti-TLT-1 antibody or a functional fragment or variant thereof comprises SEQ ID NO: 1. In another embodiment of any of the above compositions, the single chain anti-TLT-1 antibody or a functional fragment or variant thereof comprises SEQ ID NO: 2. In another embodiment of any of the above compositions, the single chain anti-TLT-1 antibody or a functional fragment or variant thereof comprises SEQ ID NO: 3.

In another embodiment of any of the above compositions, the composition further comprises one or more therapeutic agents. In a particular embodiment, the therapeutic agent is selected from chemotherapy, antibiotic therapy, surgery, anti-coagulant therapies, and anti-inflammatory therapies. In another particular embodiment, the composition further comprises one or more pharmaceutically acceptable carriers.

In another aspect, the invention teaches a method of making single chain antibodies to TLT-1, the method comprising the steps of screening a scFv library with a TLT-1 fusion protein, and selecting reactive clones and infecting *E. coli* with selected clones, thereby producing soluble scFvs.

In one embodiment of the method, the TLT-1 fusion protein consists of the extracellular domain of TLT-1 and the Fc fragment of human Fc (TLT-1-Fc). In another embodiment, the method further comprises confirming the specificity of the selected clones after step (ii) and step (iii).

In one aspect, the invention features a kit for use in modulating platelet activity, the kit comprising a single chain anti-TLT-1 antibody or a functional fragment or variant thereof, and instructions for use. In one embodiment, platelet activity is platelet aggregation.

In another aspect, the invention features a kit for use in modulating platelet aggregation, the kit comprising a single chain anti-TLT-1 antibody or a functional fragment or variant thereof, and instructions for use.

In yet another aspect, the invention features a kit for use in modulating platelet aggregation in a subject, the kit comprising a single chain anti-TLT-1 antibody or a functional fragment or variant thereof in an amount effective to modulate platelet aggregation, and instructions for use.

In another aspect, the invention features a kit for use in treating a disease or disorder associated with platelet aggregation in a subject, the kit comprising a single chain anti-TLT-1 antibody or a functional fragment or variant thereof in an amount effective to modulate platelet aggregation, and instructions for use.

In yet another aspect, the invention features a kit for use in modulating platelet aggregation in a subject at risk for a disease or disorder associated with platelet aggregation, the kit comprising a single chain anti-TLT-1 antibody or a functional fragment or variant thereof in an amount effective to modulating platelet aggregation, and instructions for use.

In another aspect, the invention features a kit for use in treating a subject at risk for a disease or disorder associated with platelet aggregation, the kit comprising a single chain anti-TLT-1 antibody or a functional fragment or variant thereof in an amount effective to modulating platelet aggregation, and instructions for use.

In yet another aspect, the invention features a kit for use in treating a subject at risk for a disease or disorder associated with platelet aggregation, the kit comprising a single chain anti-TLT-1 antibody or a functional fragment or variant thereof in an amount effective to modulate platelet aggregation, an additional therapeutic agent, and instructions for use.

In another aspect, the invention features a kit for use in treating a subject that is currently or previously being treated for a disease or disorder associated with platelet aggregation, the kit comprising a single chain anti-TLT-1 antibody or a functional fragment or variant thereof in an amount effective to modulating platelet aggregation, and instructions for use.

In yet another aspect, the invention features a diagnostic kit for the diagnosis of a disease or disorder associated with platelet aggregation in a subject comprising a single chain anti-TLT-1 antibody or fragment thereof, and written instructions for use of the kit for detection of a disease or disorder associated with platelet aggregation.

In another aspect, the invention features a kit for the detection of a soluble fragment of TLT-1 receptor, the kit comprising a single chain anti-TLT-1 antibody or a functional fragment or variant thereof in an amount effective to detect a soluble fragment of TLT-1 receptor.

In one aspect, the invention features a single chain anti-TLT-1 antibody or a functional fragment or variant thereof consisting of SEQ ID NO: 1.

In another aspect, the invention features a single chain anti-TLT-1 antibody or a functional fragment or variant thereof consisting of SEQ ID NO: 2.

In another aspect, the invention features a single chain anti-TLT-1 antibody or a functional fragment or variant thereof consisting of SEQ ID NO: 3.

In one aspect, the invention features a single chain anti-TLT-1 antibody or a functional fragment or variant thereof comprising SEQ ID NO: 1.

In another aspect, the invention features a single chain anti-TLT-1 antibody or a functional fragment or variant thereof comprising SEQ ID NO: 2.

In another aspect, the invention features a single chain anti-TLT-1 antibody or a functional fragment or variant thereof consisting of SEQ ID NO: 3.

Other single chain anti-TLT-1 antibodies or a functional fragments thereof can comprise SEQ ID NO: 3, SEQ ID NO:4 or SEQ ID NO: 5.

In a further aspect, the invention features an expression vector comprising a single chain anti-TLT-1 antibody or a functional fragment or variant thereof of any one of the above aspects. In one embodiment, an isolated host cell comprises the expression vector of any of the above aspects.

In any of the above aspects of the invention, the a platelet activity as used herein includes an activity which involves the action of platelets, including, but not limited to, platelet aggregation, adhesion to the site of a wound, activation (e.g., release of blood clotting factors), induction of blood clotting (e.g., induction of fibrin formation), inhibition of bleeding, and induction of wound healing.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2 (A-C) is a panel of three graphs showing selection of phage antibodies that bind to TLT-1. Panel A is a graph showing clones that specifically bound to TLT-1, but not to the Fc fragment, were isolated in a monoclonal phage ELISA format. For phage ELISA, TLT-1-Fc (black histogram) or Fc fragment (gray histogram) were immobilized on a microtiter plate (10 μg/ml) and incubated with purified phage preparations ($10^{11}$ phages). Binding was detected using an anti-M13 antibody-HRP conjugate. The data represented are the mean of three independent experiments. Panels B and C are graphs showing the isolated phage clones were analyzed by flow cytometry for binding to TLT-1 transfected cells and to transfection control cells (HEK293). Phages from the naïve libraries were also used as a negative control (Neg. Cl.). The histograms (Panel B) and dot blots (Panel C) for clone C10 are shown.

FIG. 3 (A-D) shows purification of soluble scFvs and analysis of binding to murine TLT-1. Panel A, left panel shows SDS-PAGE of the supernatant from C10 clone after IPTG induction (lane 1, 10 ml) and of the purified C10 scFv (lane 3, 1 μg); Panel A, right panel shows western blot of the purified scFv (lane 5) probed with an anti-His-tag antibody-HRP conjugate. Lane 2 and lane 4 are the molecular weight markers. Panel B shows SDS-PAGE of purified scFvs. Panel C is a graph showing results of analysis of scFv binding to TLT-1 in an ELISA assay. TLT-1-Fc was immobilized on a microtiter plate and incubated with purified anti-TLT-1 scFvs or with a negative control scFv (N. Cl.) (2 μg/well). Bound scFvs were detected with Protein L-HRP conjugate. Panel D is a graph showing results of analysis of TLT-1 binding to scFvs in a sandwich ELISA. Purified anti-TLT-1 scFvs or a negative control scFv were immobilized on a microtiter plate and incubated with TLT-1-Fc (30 ng/well). Binding of TLT-1-Fc was detected using anti-TLT-1 pAb. The data represented are the mean of three independent experiments.

FIG. 4 (A-D) shows binding of TLT-1 specific scFvs to human platelets. Panel A shows the results when purified scFvs (indicated with an arrow) and an irrelevant scFv were analyzed for binding to thrombin-activated platelets in flow cytometry. Panel B shows binding of scFv C10 (upper panels) and of anti-TLT-1 pAb (lower panels) to resting and thrombin-stimulated platelets analyzed by flow cytometry. Panel C shows western blot analysis of the immunoprecipitation of TLT-1 from a human platelet lysate using scFv C10 and whole platelet lysate from resting (R) and thrombin-activated (A) platelets. A control experiment was performed with an irrelevant single chain scV antibody, as indicated (Control).

Immunoprecipitates and platelet lysates were probed with anti-TLT-1 pAb. Panel D shows flow cytometric analysis of scFvs C10 and D1 compared to an irrelevant scFv (Control).

FIG. 5 (A-G) shows the effect of anti-TLT-1 antibodies on platelet aggregation. The effect of anti-TLT-1 antibodies on platelet aggregation was analyzed in an aggregrometry assay in which the inhibition of platelet aggregation is indicated by the prevention of transmission on the y-axes. Panel A shows the effect of anti-TLT-1 pAb on platelet aggregation. Platelets were activated with thrombin in the presence of vehicle, anti-TLT-1 pAb or control. The y-axis indicates increasing transmission from low to high in the direction of the arrow. Panels B-G show the effect of TLT-1 specific scFvs on platelet aggregation. Washed platelets were activated with thrombin, PMA or collagen in the presence of vehicle, or an irrelevant scFv (Negative (Neg.) clone 1), or anti-TLT-1 scFvs (C10 and D1). Data are representative of three independent experiments using platelets from different donors. The y-axis indicates increasing transmission from low to high in the direction of the arrow.

FIG. 6 shows the sequences corresponding to SEQ ID NOs 1-6. SEQ ID NO: 1 corresponds to GenBank Accession No. DQ375453. SEQ ID NO: 2 corresponds to GenBank Accession No. DQ375449. SEQ ID NO: 3 corresponds to GenBank Accession No. DQ375451. SEQ ID NO: 4 corresponds to GenBank Accession No. DQ375450. SEQ ID NO: 5 corresponds to GenBank Accession No. DQ375452. SEQ ID NO: 6 corresponds to GenBank Accession No. DQ375454.

Figure 7:
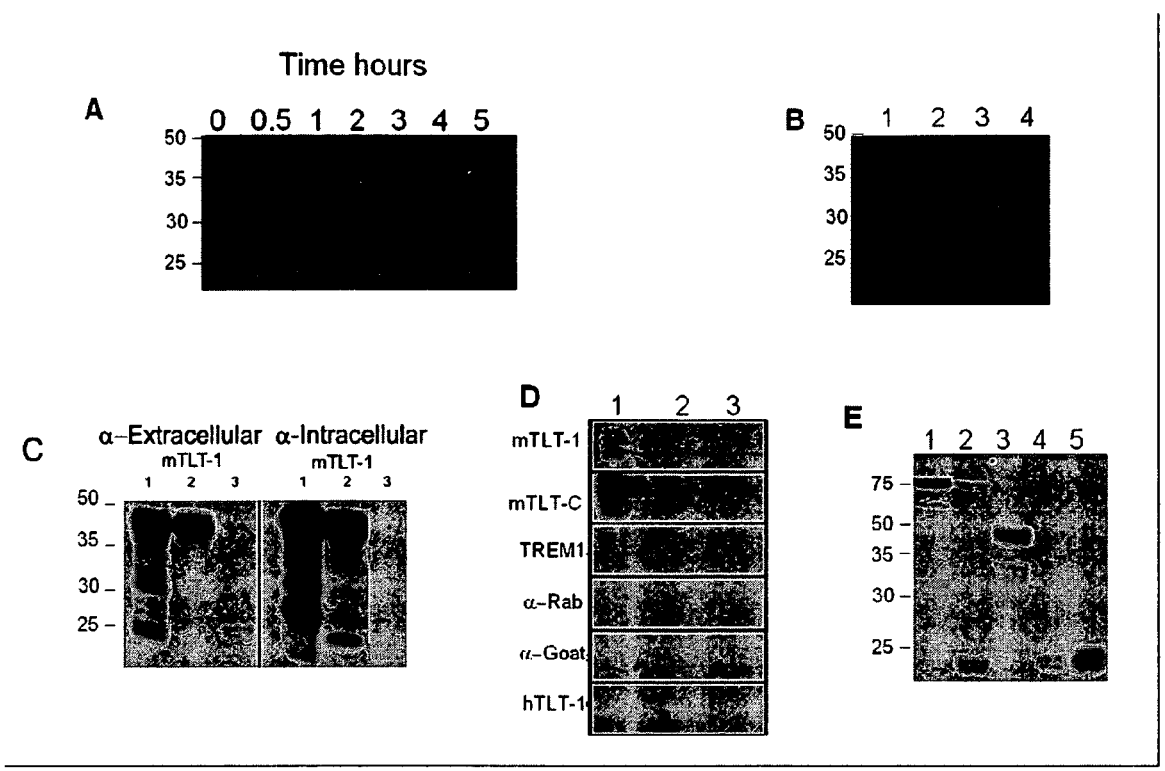

FIG. 7 (A-E) shows Western blot analysis for the detection of soluble fragment of TLT-1 in murine platelets, serum, and mTLT-1 transfected HEK293 cells. All samples were separated by SDS-PAGE under reducing conditions. Panel A shows results of Western Blot. Murine platelets ($1.5 \times 10^7$) were activated for the time indicated above each lane. Membranes were probed with an a-mTLT-1 antibody specific for the extracellular domain. Panel B shows results of Western Blot. Resting or activated platelets ($1.5 \times 10^9$) in Tyrode's buffer were pelleted by centrifugation. Lanes 1 and 3 represent 30 mg of total protein from the pellet. Lanes 2 and 4 represent 20 ml of the supernatant. Panel C shows results of Western Blot. Lane 1, 30 µg of total protein from pelleted resting murine platelets. Lane 2, activated platelets. Lane 3, 5 µl of murine serum. Samples were probed with an antibody specific for either the extracellular domain of murine TLT-1 (left panel) or intracellular domain of human TLT-1 (right), which cross-reacts with the intracellular domain of mTLT-1. Panel D shows results of Western Blot. Lane 1, 5 µl of murine serum. Lane 2, 5 µl of murine plasma. Lane 3, 5 µl of defibrinated murine plasma. Samples were probed with various antibodies. From top to bottom: two antibodies (mTLT-1 and mTLT-C, C-commercial) specific to the extracellular domain of mTLT-1, antibodies specific for TREM-1, the secondary anti-Rabbit Fc (α-Rab) alone, anti-goat Fc alone (α-Goat), and hTLT-1-specific antibodies. Panel E shows results of Western Blot. Lanes 1-4: 30 µg total protein from mTLT-1 HEK293 cell pellet, or conditioned culture media. Lane 1, Cell-associated mTLT-1/YFP. Lane 2, soluble mTLT-1 isoform released from cells transfected with mTLT-1/YFP. Lane 3, cell-associated mTLT-1. Lane 4, soluble mTLT-1 isoform released from cells transfected with mTLT-1. Lane 5, 5 µl of murine serum.

Figure 8:
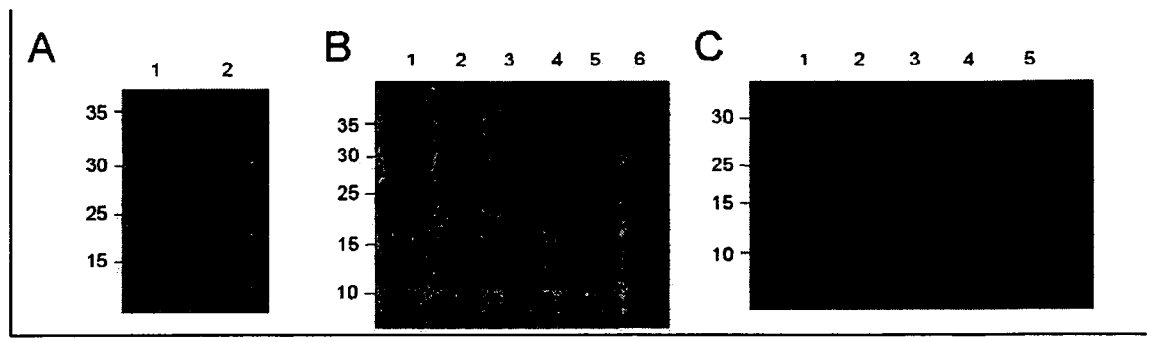

FIG. 8 (A-C) Western blot analysis for the detection of extracellular domain of TLT-1 in human platelets, serum and the recombinant HEK293 cells. All samples were separated by SDS-PAGE under reducing conditions and probed with an antibody specific for the extracellular domain of hTLT-1. Panel A shows results of Western Blot. Lane 1, 30 µg total protein from a pellet of activated human platelets. Lane 2, 3 µl of human serum. Panel B shows results of Western Blot. Resting or activated platelets ($1.5 \times 109$) in Tyrode's buffer were pelleted by centrifugation. Lanes 1 and 3 represent 30 µg total protein from resting and activated platelets. Lanes 2 and 4 represent 20 µl of the supernatant. Lane 5, 5 µl of human plasma. Lane 6, 5 µl of human serum. Panel C shows results of Western Blot. Wild-type and recombinant HEK293 cells were pelleted by centrifugation. Lanes 1 and 3 represent 30 µg total protein from pelleted wild type and TLT-1 transfected HEK293 cells. Lanes 2 and 4 represent 20 µl of supernatant from wild-type and TLT-1 transfected HEK293 cells. Lane 5, 20 µl of supernatant from thrombin-activated platelets for comparison.

DETAILED DESCRIPTION OF THE INVENTION

The present invention relates to methods and compositions for modulating platelet aggregation, and methods and compositions for treating a disease or disorder associated with platelet aggregation in a subject, comprising administering a single chain TREM-like transcript-1 (TLT-1) antibody or a functional fragment or variant thereof in an amount effective to modulate platelet aggregation.

Recently, a TREM family member called TREM like transcript (TLT)-1 from both mice and humans has been cloned (9). Murine TLT-1 (mTLT-1) is abundantly expressed only on platelets and megakaryocytes; and both mTLT-1 and human TLT-1 (hTLT-1) are sequestered in the platelet alpha granules, and quickly translocated to the platelet surface upon platelet activation (9, 10). Thus, the specificity and regulation of TLT-1 expression suggests that it plays a unique role in homeostasis, making it an attractive tool for the dissection and manipulation of platelet function (10).

Recent work with the triggering receptor expressed in myeloid cells (TREM)-1 has shown that protein derivatives of the TREM-1 extracellular domain are effective in treating murine models of sepsis, making TREM-1 an appealing candidate drug target. Studies using a murine model of septic shock have demonstrated an interesting paradigm for TREM-1 function: Expression of surface-bound TREM-1 is upregulated in response to bacterial infection, resulting in increased production of pro-inflammatory cytokines and leading to an immune response against the potential pathogen. Gibot et al. demonstrated that a 17 amino acid peptide derived from TREM-1 (LP17) was able to protect mice from both lipopolysaccharide (LPS) and cecal ligation-induced shock. Multiple lines of evidence now suggest an important role for the Triggering Receptors Expressed on Myeloid cells (TREM) in the regulation of the septic response. TREM-Like Transcript (TLT)-1 is clustered with the TREM on chromosome 6 but has distinct biochemical characteristics and is expressed only on platelets and megakaryocytes.

DEFINITIONS

Unless defined otherwise, all technical and scientific terms used herein have the meaning commonly understood by one of ordinary skill in the art to which this invention belongs. The following references can provide one of skill in the art to which this invention pertains with a general definition of many of the terms used in this invention, and can be referenced and used so long as such definitions are consistent with the meaning commonly understood in the art: Singleton et al., Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, $2^{nd}$ Edition, W. B. Saunders Company. Any additional technical resources available to the person of ordinary skill in the art providing definitions of terms used herein having the meaning commonly understood in the art can be consulted. For the purposes of the present invention, the following terms are further defined. Additional terms are defined elsewhere in the description.

In this disclosure, the terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "antibody" is meant to include any immunoglobulin polypeptide, or fragment thereof, having immunogen binding ability.

The term "administration" or "administering" is meant to include an act of providing a compound or pharmaceutical composition of the invention to a subject in need of treatment.

The term "A1" is meant to refer to a single chain antibody corresponding to GenBank accession No. DQ375449.

The term "A7" is meant to refer to a single chain antibody corresponding to GenBank accession No. DQ375450.

The term "A8" is meant to refer to a single chain antibody corresponding to GenBank accession No. DQ375451.

The term "B8" is meant to refer to a single chain antibody corresponding to GenBank accession No. DQ375452.

The term "D1" is meant to refer to a single chain antibody corresponding to GenBank accession No. DQ375454.

The term "C10" is meant to refer to a single chain antibody corresponding to GenBank accession No. DQ375453.

The term "cancer" is meant to refer to a disease that is caused by, or results in, inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The term "cardiovascular disease" is meant to refer to any refers to any disease that affects the cardiovascular system. Cardiovascular disease can include, but is not limited to, heart disease, heart attack, atherosclerosis, and stroke.

The term "decrease" is meant a negative alteration. For example, a reduction by at least about 5% relative to a reference level. An exemplary decrease may be by 5%, 10%, 15%, 20%, 25% or 50%, or even by as much as 75%, 85%, 95% or more.

The term "effective amount" or "amount effective" is an amount sufficient to effect a beneficial or desired clinical result. An effective amount can be administered in one or more doses. In terms of treatment, an effective amount is amount that is sufficient to palliate, ameliorate, stabilize, reverse or slow the progression of the disease, or otherwise reduce the pathological consequences of the disease. In terms of an adjuvant, an effective amount is one sufficient to enhance the immune response to the immunogen. The effective amount is generally determined by the physician on a case-by-case basis and is within the skill of one in the art. Several factors are typically taken into account when determining an appropriate dosage. These factors include age, sex and weight of the patient the condition being treated, the severity of the condition and the form of the antibody being administered. For instance, the concentration of scFv need not be as high as that of native antibodies in order to be therapeutically effective.

The term "fragment" is meant a portion of a protein or nucleic acid that is substantially identical to a reference protein or nucleic acid. In some embodiments, the fragment is a fragment of a single chain antibody. In some embodiments the portion retains at least 50%, 75%, or 80%, or more preferably 90%, 95%, or even 99% of the biological activity of the reference protein or nucleic acid described herein. In other embodiments, the fragment comprises at least 5, 10, 11, 12, 13, 14, 15, 16, 17, 18, 19, or 20 amino acids of a reference protein or is a nucleic acid molecule encoding such a fragment. In certain embodiments, the fragment in a soluble fragment. In specific examples, the soluble fragment corresponds to the extracellular domain of murine or human TLT-1.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The term "increase" is meant to refer to a positive alteration. For example, a positive alteration by at least about 5% relative to a reference level. An exemplary increase may be by 5%, 10%, 15%, 20%, 25% or 50%, or even by as much as 75%, 85%, 95% or more.

The term "inflammatory disease" is meant to refer to a disease or disorder characterized by inflammation. In general, the inflammatory response is characterized by the release of chemicals, including but not limited to histamine, bradykinin, serotonin, and others, by damaged tissue in response to bacteria, trauma, toxins, heat, or other insult. A number of cytokines are involved in the immune response. Among the primary physical effects of the inflammatory response is for blood circulation to increase around the affected area. In particular, the blood vessels around the site of inflammation dilate, allowing increased blood flow to the area. In exemplary embodiments, inflammatory diseases are associated with platelet aggregation. Exemplary inflammatory diseases can include vascular inflammation or systemic inflammatory syndromes, for example sepsis.

The term "inhibit" is meant a decrease, suppression, attenuation, arrest, or stabilization in a response, or in the development or progression of a disease.

The term "mediate" or "mediated" is meant to refer to

The term "microtiter plate assay" is meant to refer to a test that is carried out in a microtiter plate (e.g. a flat plate with multiple wells, a 6 well, 24 well, 96 well plate). A microtiter plate is amenable to use in a high throughput format. In certain examples, a "microtiter plate assay" is meant to refer to a test that can detect modulation of platelet aggregation, for example, by an agent such as a TLT-1 antibody or fragments thereof. An exemplary microtiter plate assay is described by Moran N. et al. Analy Biochem. 357: 77-84. 2006, incorporated by reference in its entirety herein.

The term "modulation" is meant any alteration (e.g., increase or decrease; activation or inhibition) in a biological function or activity. In preferred embodiments, modulation is meant to refer to an alteration, for example an increase or a decrease, in platelet aggregation.

The term "platelet", also referred to as a "thrombocyte", refers to nucleus-free cytoplasmic fragments derived from large cells in the bone marrow, the megakaryocyte. The central portion of a platelet stains purple with Wright's stain and is referred to as the granulomere. The peripheral portion stains clear and is called the hyalomere. Normal platelet counts range from 150,000 to 400,000 per cu/mm blood.

The term "platelet aggregation" refers to the clumping together of platelets in the blood. Platelet aggregation is part of the sequence of events that leads to the formation of a thrombus. Platelets play a crucial part in the blood clotting process by forming a platelet plug. This is a two-step process. First, single platelets bind to the site of the wound (adhesion). Next, the platelets bind to each other (activation). Activation can be stimulated by components released when the blood vessel is damaged and by thrombin, released during the blood clotting process. When platelets become activated they change. They release agents which recruit and activate the surrounding platelets. The result of these two processes is the formation of fibrin which stabilizes the platelet plug, stops bleeding and allows injuries to heal.

The term "platelet-associated disorder" includes a disorder, disease or condition which is caused, characterized by, related to, or associated with a misregulation (e.g., downregulation or upregulation) of platelet activity. Platelet associated disorders also include disorders, diseases, or conditions which can be improved and/or treated by modulation of platelet activity. Platelet-associated disorders can detrimentally affect cellular functions such as blood-clotting, as well as other functions such as cellular proliferation, growth, differentiation, or migration, inter- or intra-cellular communication, tissue function, and systemic responses in an organism, such as immune responses. Preferred examples of platelet-associated disorders include, but are not limited to, inflammatory disorders, including sepsis, immune disorders, cancer (e.g., leukemias such as acute megakaryocytic leukemia, megakaryoblastic leukemia), infectious disease, cardiovascular diseases, including stroke, heart disease, atherosclerosis, myocardial infarction, vascular disorders, arteriosclerosis, clotting and/or bleeding disorders, platelet insufficiency, and TLT-1 associated disorders.

The term "platelet aggregation test" refers to a test to measure the rate and degree to which dispersed platelets in a sample of plasma (the liquid portion of blood) form clumps after the addition of a material that normally stimulates aggregation.

The term "reference" is meant to include a standard or control condition.

The term "single chain antibody" ("scFv") refers to single polypeptide chain binding proteins having the characteristics and binding ability of multi chain variable regions of antibody molecules. Single chain V region fragments are made by linking L and/or H chain V regions by using a short linking peptide, as described in Bird et al. (1988) Science 242:423 426.

The term "subject" is meant a mammal, such as a human patient or an animal (e.g., a rodent, bovine, equine, porcine, ovine, canine, feline, or other domestic mammal).

The term "thrombin" refers to a coagulation protease. Thrombin is a serine protease (EC 3.4.21.5) that is produced by the enzymatic cleavage of two sites on prothrombin by activated Factor X (Xa). Thrombin converts soluble fibrinogen into insoluble strands of fibrin.

The term "TREM-like Transcript-1" TLT-1 refers to a novel platelet membrane receptor that is expressed exclusively in platelets and megakaryocytes. Expression is upregulated upon platelet activation. Exemplary biological activities of TLT-1 include: 1) interaction with a TLT-1 target molecule (e.g., a second TLT-1 molecule, or a non-TLT-1 molecule such as a TLT-1 specific antibody, a TLT-1 ligand, a cell-surface protein, a Src family member, Src Homology Domain containing Phosphatase 1 (SHP)-1, SHP-2 Src Homology Domain containing Phosphatase 2, SHIP-1 Src Homology Domain containing Inositol Phosphatase 1, an SH2 domain containing protein, an SH3 domain containing protein, and/or a WW domain containing protein); 2) modulation of megakaryocyte differentiation; 3) modulation of platelet differentiation and/or production (thrombopoiesis); 4) modulation of platelet activity; 5) modulation of intra- or inter-cellular signaling; 6) localization to platelet and/or megakaryocyte alpha granules: 7) modulation of platelet and/or megakaryocyte granule formation and/or sorting; 8) localization to the platelet and/or megakaryocyte cell surface; 9) modulation of platelet interaction with and/or adhesion to the extracellular matrix and/or basement membrane; 10) modulation of blood clotting; 11) modulation of bleeding; 12) modulation of immune responses; 13) modulation of activation of neutrophils and/or other leukocytes; 14) modulation of dendritic cell maturation and/or function; and/or 15) modulation of cellular proliferation.

The term "treat" or "treating" is meant stabilize, reduce, or ameliorate the symptoms of any disease or disorder.

The term "vector" is meant to refer to a nucleic acid molecule, for example, a plasmid, cosmid, or bacteriophage, which is capable of replication in a host cell. In one embodiment, a vector is an expression vector comprising a single chain TLT-1 antibody or a functional fragment or variant thereof. Typically, expression is placed under the control of certain regulatory elements, including constitutive or inducible promoters, tissue-preferred regulatory elements, and enhancers.

The term "washed sample" is meant to refer to a sample of platelets that have been prepared for further assay or testing by processing in a buffer solution. Various platelet washing methods are known in the art. In exemplary embodiments, platelets can be washed in buffer solution, for example a HEPES [N-2-hydroxyethylpiperazine-N'-2-ethanesulfonic acid]buffer. In certain examples, the buffer for washing is Tyrode's buffer (10 mM HEPES [N-2-hydroxyethylpiperazine-N'-2-ethanesulfonic acid], 138 mM NaCl, 5.5 mM glucose, 2.9 mM KCl, and 12 mM NaHCO3, pH 7.4) or Tyrode's solution (2 mM MgCl2, 137 mM NaCl, 2.68 mM KCl, 3 mM NaH2PO4, 0.1% glucose, 5 mM HEPES, and 0.35% albumin, pH 7.35).

Antibodies

The invention provides the use of antibodies that react with TREM-Like Transcript (TLT)-1. US Patent Application Publication 2004/0180409 describes TLT-1 antibodies, and is incorporated herein by reference in its entirety. In preferred embodiments of the instant invention, the antibodies are single chain antibodies.

Methods for production of antibodies are known by those skilled in the art. If polyclonal antibodies are desired, a selected mammal (e.g., mouse, rabbit, goat, horse, etc.) is immunized with an immunogenic polypeptide bearing an epitope(s) from a polypeptide. Serum from the immunized animal is collected and treated according to known procedures. Various adjuvants known in the art can be used to enhance antibody production. (for further details see for example: Using Antibodies, A Laboratory Manual, edited by Harlow, E. and Lane, D., 1999, Cold Spring Harbor Laboratory Press, (e.g. ISBN 0-87969-544-7)). If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order to generate a larger immunogenic response, polypeptides or fragments thereof maybe haptenised to another polypeptide for use as immunogens in animals or humans.

For isolation of the antibodies, the immunoglobulins in the culture supernatants or in the ascitic fluid can be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the target antigen, or with Protein-A.

Monoclonal antibodies can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Techniques for the production and isolation of monoclonal antibodies and antibody fragments are well-known in the art, and are additionally described, among other places, in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

Preferred epitopes include regions of TLT-1 that are located on the surface of the protein, e.g. hydrophilic regions, as well as regions with high antigenicity. Studies of the crystal structure of TLT-1 have shed light on preferred epitope regions.

Crystal structures of the previously determined immunoglobulin-like domains from several TREM family receptors include NKp44 (PDB code 1HKF) (5), murine TREM-1 (mTREM-1) (1U9K)(6), and two crystal structures of human TREM-1 (hTREM-1)(1Q8M, 1SMO)(7; 8). Recently, TREM-1 and TREM-2 gained attention because of their potential involvement in human diseases. The structure of TLT-1 is similar to other immunoglobulin-like variable domains, particularly those of triggering receptor expressed on myeloid cells-1 (TREM-1), the natural killer cell-activating receptor NKp44, and the polymeric immunoglobulin receptor (22). The immunoglobulin-like domain of human TLT-1 (hTLT-1) consists of 105 residues, and is attached to the membrane by a 37-amino acid stalk. A recent study showed that administration of either the intact immunoglobulin-like domain of murine TREM-1, or a specific 17-amino acid peptide fragment of mTREM-1 resulted in decreased production of proinflammatory cytokines (Gibot et al 2004).

More specifically, complementarity determining regions (CDRs) have been identified in antibody V domains as portions as antigen binding regions (38). In single-domain immunoglobulin-like molecules, the CDR equivalent loops are referred to as CDR1, 2, and 3. The structure of hTLT-1 demonstrates variability in these loop structures and these are the locations of the largest structural differences between hTLT-1 and related immunoglobulin-like crystal structures. Accordingly, CDR loops may provide potentially favorable epitope regions. Possible epitopes of TREM family may be found in the CDR2-equivalent residues that link the C and C' loop that connects the two beta strands. The second hypervariable region in the TREM family includes CDR2-equivalent residues, linking strands βC' and βC". In murine and human TREM-1, NKp44, and pIgR, this hyper-variable region extends from the end of βC', through strand βC" to R76, located in the C"-D loop (22). In TLT-1, conserved residues surrounding CDR2 include S65 (serine or threonine in related molecules) and R76. The hydrogen bond between a side chain equivalent to S65 and a backbone atom of strand βC is maintained in all known structures of TREM family members. R76, in turn, forms a hydrogen bond and a salt bridge with the side chains of Q95 and D98 from the nearby loop D-E. These interactions likely stabilize the overall structure of the β-sheets, while allowing sequence diversity within the hypervariable loops. Thus, this region may be a potential target for antibody design.

Other possible epitopes of TREM family may be found in the third CDR-equivalent loop. The third CDR-equivalent loop is very short and consists of only 4 residues that do not show hydrogen bonds characteristic of β-strands (22). This loop shows the greatest conformational variability between TREM-1, NKp44, and TLT-1 (the only TREM family structures currently known).

Although antibodies useful in practicing the invention can be polyclonal or monoclonal, single chain antibodies are preferred. The invention encompasses single chain V region fragments ("scFv") of anti TLT-1.

Phage display of single chain Fv (scFv) offers a new way to produce monoclonal antibodies with defined binding specificities (13, 14). In screening phage display libraries, for example, the phage express scFv fragments on the surface of their coat with a large variety of complementarity determining regions (CDRs). This technique is well known in the art. In particular embodiments, phage-displayed human antibody library are used to derive scFvs specific for TLT-1. A repertoire of many different scFvs can be displayed on the surface of filamentous bacteriophage, allowing phages with a specific antigen-binding activity to be selected by panning on the target antigen (13). This approach has several advantages compared to the traditional hybridoma technology; (i) monoclonal antibodies can be isolated faster and without the need for animal immunization (23); (ii) the use of a naïve library (derived from non-immunized donors) allows the selection of antibodies against self-antigen and weakly immunogenic proteins (17, 24) (iii) scFvs can be efficiently and economically produced in bacteria or in other expression systems (25, 26). ScFv antibodies contain the variable regions of heavy and light chains connected by a linker peptide and represent the smallest units retaining the antigen-binding specificity of whole IgGs (15). Importantly, when these antibody fragments are of human origin, adverse immune responses in human therapy can be minimized (16, 17). Given that methods for the preparation of genetic sequences, their replication, their linking to expression control regions, formation of vectors therewith and transformation of appropriate hosts are well understood techniques, it would indeed be greatly advantageous to be able to produce, by genetic engineering, single polypeptide chain binding proteins having the characteristics and binding ability of multi chain variable regions of antibody molecules. Single chain V region fragments are made by linking L and/or H chain V regions by using a short linking peptide, as described in Bird et al. (1988) Science 242:423 426. Any peptide having sufficient flexibility and length can be used as a linker in a scFv. Usually the linker is selected to have little to no immunogenicity. An example of a linking peptide is (GGGGS).sub.3(SEQ ID NO: 37), which bridges approximately 3.5 nm between the carboxy terminus of one V region and the amino terminus of another V region. Other linker sequences can also be used, and can provide additional functions, such as a means for attaching a drug or a solid support. Techniques have been described for the production of single chain antibodies (see, e.g., U.S. Pat. No. 4,946,778, and U.S. Pat. No. 7,115,722).

All or any portion of the H or L chain can be used in any combination. Typically, the entire V regions are included in the scFv. For instance, the L chain V region can be linked to the H chain V region. Alternatively, a portion of the L chain V region can be linked to the H chain V region, or a portion thereof. Also contemplated are scFvs in which the H chain V region is from H11, and the L chain V region is from another immunoglobulin. It is also possible to construct a biphasic, scFv in which one component is a H11 polypeptide and another component is a different polypeptide, such as a T cell epitope.

The scFvs can be assembled in any order, for example, $V_H$-(linker)-$V_L$ or $V_L$-(linker)-$V_H$. Tandem scFvs can also be made, such as (X)-(linker)-(X)-(linker)-(X), in which X are TLT-1 polypeptides, or combinations of TLT-1 with other polypeptides. In another embodiment, single chain antibody polypeptides have no linker polypeptide, or just a short, inflexible linker. Exemplary configurations include $V_L$-$V_H$ and $V_H$-$V_L$. The linkage is too short to permit interaction between $V_L$ and $V_H$ within the chain, and the chains form homodimers with a $V_L$/$V_H$ antigen binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.).

Expression conditions should ensure that the scFv assumes functional and, preferably, optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scFv in prokaryotic systems; or, it may be preferably to express scFv in eukaryotic cells.

Preferred scFv comprise at least 5, 15, 15, 20, 25, 30 or more consecutive amino acids that react with TLT-1.

In a particular embodiment of the invention, antibodies which are directed against epitopes from TREM-Like Transcript (TLT)-1 are useful in prophylactic treatment, for example, in a patient before a surgical procedure.

In another particular embodiment, neutralizing and blocking antibodies are useful in the methods of the invention.

In certain embodiments of the invention, the single chain anti-TLT-1 antibody comprises a functional fragment thereof that has specificity to TLT-1. More specifically, the single chain anti-TLT-1 antibody or a functional fragment thereof has specificity to the extracellular domain of TLT-1. In other certain embodiments, the single chain anti-LT-1 antibody or a functional fragment thereof is a full-length antibody. In particular examples, the single chain antibody is monoclonal.

In particular embodiments of the invention, the single chain anti-TLT-1 antibody or a functional fragment thereof is SEQ ID NO: 1. The single chain anti-TLT-1 antibody or a functional fragment thereof can comprise SEQ ID NO: 1, shown below:

```
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGGTATTTCTTCTACTGGTGGTGCTACAACTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

TCTACTTATGATTTTGATTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTTGCCGGGCAAGTCAGAGCATTAGCAGCTATTT

AAATTGGTATCAGCAGAAACCAGGGAAAGCCCCTAAGCTCCTGATCTATG

GTGCATCCACTTTGCAAAGTGGGGTCCCATCAAGGTTCAGTGGCAGTGGA

TCTGGGACAGATTTCACTCTCACCATCAGCAGTCTGCAACCTGAAGATTT

TGCAACTTACTACTGTCAACAGAATGCTGATGCTCCTACTACGTTCGGCC
```

```
AAGGGACCAAGGTGGAAATCAAACGGGCGGCCGCACATCATCATCACCAT

CACGGGGCCGCAGAACAAAAACTCATCTCAGAAGAGGATCTGAATGGGGC

CGCATAG
```

In other examples, the single chain anti-TLT-1 antibody or a functional fragment thereof is SEQ ID NO: 2. The single chain anti-TLT-1 antibody or a functional fragment thereof can comprise SEQ ID NO: 2, shown below:

```
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGGTATTGGTACTACTGGTTATGCTACAGCTTACGCAGACTCCGTGAA

GGGCAGGTTCACCATCTCCAGAGACAATTCCAAGAACACGCTGTATCTGC

AAATGAACAGCCTGAGAGCCGAGGACACGGCCGTATACTACTGTGCGAAA

GGTAATTGGTTTTGACTACTGGGGCCAGGGAACCCTGGTCACCGTCTCGA

GCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATACT

GCATCCACCTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAACAGTCTAGTACTGATCCTGGTACGTTCGGCCAA

GGGACCAAGGTGGAAATCAAACGGGCGGCCGCACATCATCATCACCATCA

CGGGGCCGCAGAACAAAAACTCATCTCAGAAGAGGATCTGAATGGGGCCG

CATAG
```

In other examples, the single chain anti-TLT-1 antibody or a functional fragment thereof is SEQ ID NO: 3. The single chain anti-TLT-1 antibody or a functional fragment thereof can comprise SEQ ID NO: 3, shown below:

```
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGGAGCT

ATGCCATGAGCTGGGTCCGCCAGGCTCCAGGGAAGGGGCTGGAGTGGGTC

TCAGGTATTGGTACTACTGGTTATAGTACAGCTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

ACTGCTTATACTTTTGACTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTTGCCGGGCAAGTCAGAGCATTAGCAGCTATTT

AAATTGGTATCAGCAGAAACCAGGGAAAGCCCCTAAGCTCCTGATCTATT

CTGCATCCACTTTGCAAAGTGGGGTCCCATCAAGGTTCAGTGGCAGTGGA

TCTGGGACAGATTTCACTCTCACCATGAGCAGTCTGCAACCTGAAGATTT
```

```
TGCAACTTACTACTGTCAACAGAATAGTACTTATCCTGCTACGTTCGGCC

AAGGGACCAAGGTGGAAATCAAACGGGCGGCCGCACATCATCATCACCAT

CACGGGGCCGCAGAACAAAAACTCATCTCAGAAGAGGATCTGAATGGGGC

CGCATAG
```

Additional sequences are represented by SEQ ID NOs: 4, 5, and 6 as shown below:

```
                                          SEQ ID NO: 4
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGCTATTGGTAGTTATGGTTCTGCTACAGCTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

AATGGTTATGATTTTGACTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTTGCCGGGCAAGTCAGAGCATTAGCAGCTATTT

AAATTGGTATCAGCAGAAACCAGGGAAAGCCCCTAAGCTCCTGATCTATA

ATGCATCCGGTTTGCAAAGTGGGGTCCCATCAAGGTTCAGTGGCAGTGGA

TCTGGGACAGATTTCACTCTCACCATCAGCAGTCTGCAACCTGAAGATTT

GCAACTTACTACTGTCAACAGTCTGCTGCTAATCCTTCTACGTTCGGCCA

AGGGACCAAGGTGGAAATCAAACGGGCGGCCGCACATCATCATCACCATC

ACGGGGCCGCAGAACAAAAACTCATCTCAGAAGAGGATCTGAATGGGGCC

GCATAG

SEQ ID NO: 5
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAAATATTACTGCTAGTGGTTATGCTACAGCTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

ACTACTGCTACTTTTGACTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTTGCCGGGCAAGTCAGAGCATTAGCAGCTATTT

AAATTGGTATCAGCAGAAACCAGGGAAAGCCCCTAAGCTCCTGATCTATG

ATGCATCCAATTTGCAAAGTGGGGTCCCATCAAGGTTCAGTGGCAGTGGA

TCTGGGACAGATTTCACTCTCACCATCAGCAGTCTGCAACCTGAAGATTT

TGCAACTTACTACTGTCAACAGGATACTGCTTCTCCTTCTACGTTCGGCC
```

-continued
AAGGGACCAAGGTGGAAATCAAACGGGCGGCCGCACATCATCATCACCAT

CACGGGGCCGCAGAACAAAAACTCATCTCAGAAGAGGATCTGAATGGGGC

CGCATAG

SEQ ID NO: 6
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGCTATTGGTACTACTGGTTATGCTACAGCTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

GCTAATTCTTATTTTGACTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTGCCGGGCAAGTCAGAGCATTAGCAGCTATTTA

AATTGGTATCAGCAGAAACCAGGGAAAGCCCCTAAGCTCCTGATCTATAG

TGCATCCACTTTGCAAAGTGGGGTCCCATCAAGGTTCAGTGGCAGTGGAT

CTGGGACAGATTTCACTCTCACCATCAGCAGTCTGCAACCTGAAGATTTT

GCAACTTACTACTGTCAACAGGATTCTACTTCTCCTGATACGTTCGGCCA

AGGGACCAAGGTGGAAATCAAACGGGCGGCCGCACATCATCATCACCATC

ACGGGGCCGCAGAACAAAAACTCATCTCAGAAGAGGATCTGAATGGGGCC

GCATAG

Antibodies according to the invention may be used in a method of modulating platelet activity as defined herein, the method comprising contacting cells with a single chain anti-TLT-1 antibody or a functional fragment thereof.

Antibodies according to the invention may be used in a method of modulating platelet aggregation comprising contacting cells with a single chain anti-TLT-1 antibody or a functional fragment thereof.

Antibodies may be used in a method of treating a disease or disorder associated with platelet activity in a subject, the method comprising administering to the subject a single chain anti-TLT-1 antibody or a functional fragment thereof in an amount effective to modulate platelet activity, thereby treating a disease or disorder associated with platelet activity.

Antibodies may be used in a method of treating a disease or disorder associated with platelet aggregation in a subject, the method comprising administering to the subject a single chain anti-TLT-1 antibody or a functional fragment thereof in an amount effective to modulate platelet aggregation, thereby treating a disease or disorder associated with platelet aggregation.

Antibodies may be used in a method of modulating platelet aggregation in a subject at risk for a disease or disorder associated with platelet activity, the method comprising administering to the subject a single chain anti-TLT-1 antibody or a functional fragment thereof in an amount effective to modulate platelet activity, thereby modulating platelet activity in the subject.

Antibodies may be used in a method of modulating platelet aggregation in a subject at risk for a disease or disorder associated with platelet aggregation, the method comprising administering to the subject a single chain TLT-1 antibody or a functional fragment thereof in an amount effective to modulate platelet aggregation, thereby modulating platelet aggregation in the subject.

Antibodies may be used in a method of treating a subject at risk for a disease or disorder associated with platelet activity, the method comprising administering to the subject a single chain anti-TLT-1 antibody or a functional fragment thereof in an amount effective to modulate platelet activity, thereby treating the subject.

Antibodies may be used in a method of treating a subject at risk for a disease or disorder associated with platelet aggregation, the method comprising administering to the subject a single chain anti-TLT-1 antibody or a functional fragment thereof in an amount effective to modulate platelet aggregation, thereby treating the subject.

Further, antibodies may be used in a method of diagnosing a subject as having, or having a propensity to develop, a disease or disorder associated with platelet activity, the method comprising determining the level of a soluble fragment of TLT-1 receptor in a subject, wherein an increased level of soluble TLT-1 receptor relative to the level in a reference indicates that the subject has or has a propensity to develop a disease or disorder associated with platelet activity.

Further, antibodies may be used in a method of diagnosing a subject as having, or having a propensity to develop, a disease or disorder associated with platelet aggregation, the method comprising determining the level of a soluble fragment of TLT-1 receptor in a subject, wherein an increased level of soluble TLT-1 receptor relative to the level in a reference indicates that the subject has or has a propensity to develop a disease or disorder associated with platelet aggregation.

A platelet activity as used herein includes an activity which involves the action of platelets, including, but not limited to, platelet aggregation, adhesion to the site of a wound, activation, induction of blood clotting, inhibition of bleeding, and induction of wound healing.

Diseases or Disorders

In general, methods and compositions of the invention can be used in treatment and diagnosis of diseases or disorders that are associated with platelet aggregation.

The methods of the invention can be used to treat a disease or disorder associated with platelet activity. In preferred embodiments, the disease or disorder associated with platelet activity is platelet aggregation. As used herein, a "platelet-associated disorder" includes a disorder, disease or condition which is caused, characterized by, related to, or associated with a misregulation (e.g., downregulation or upregulation) of platelet activity. Platelet associated disorders also include disorders, diseases, or conditions which can be improved and/or treated by modulation of platelet activity. Platelet-associated disorders can detrimentally affect cellular functions such as blood-clotting, as well as other functions such as cellular proliferation, growth, differentiation, or migration, inter- or intra-cellular communication, tissue function, and systemic responses in an organism, such as immune responses. Preferred examples of platelet-associated disorders include, but are not limited to cardiovascular diseases or disorders, inflammatory diseases or disorders, immune diseases or disorders, cancers (e.g., leukemias such as acute megakaryocytic leukemia, megakaryoblastic leukemia, occult thrombosis), infectious disease, stroke, heart disease, myocardial infarction, vascular disorders, arteriosclerosis, clotting and/or bleeding disorders, platelet insufficiency, and TLT-1 associated disorders.

Further examples of clotting and/or bleeding disorders include, but are not limited to, Hemophilia A (Factor VIII deficiency), Hemophilia B (Factor IX deficiency), von Willebrand disease, beta.-thalassemia, deep-vein thrombosis, thrombocytopenia, Immune Thrombocytopenic Purpura, Idiopathic Thrombocytopenic Purpura, Thrombotic Thrombocytopenic Purpura, hypercoagulation, hypocoagulation, protein S deficiency, protein C deficiency, Factor V Leiden, thrombosis, superficial vein thrombosis, phlebitis, thrombophlebitis, Factor XI deficiency (Rosenthal Syndrome or Plasma Thromboplastin Antecedent (PTA) deficiency), Factor XII deficiency (Hageman factor deficiency), Vitamin K deficiency, generalized coagulopathy, Factor XIII deficiency, Factor VII deficiency, internal bleeding, gastrointestinal bleeding, intracranial bleeding, pulmonary embolism, Afibrinogenemia, Dysfibrinogenemia, Factor II disorders, Factor III (tissue factor) associated disorders, Factor V (labile factor) deficiency, Factor X deficiency, Factor V & VIII Combined Deficiency, Factor VIII & IX combined Deficiency, Factor IX & XI Combined Deficiency, Thrombophilia (Antithrombin III deficiency), Giant Platelet Syndrome (platelet glycoprotein Ib deficiency), Fletcher Factor Deficiency (Prekallikrein deficiency), Autosomal dominant macrothrombocytopenia, the May-Hegglin anomaly, Sebastian syndrome, Fechtner syndrome, platelet storage pool deficiency, Chediak-Higashi syndrome, amegakaryocytic thrombocytopenia, thrombocytopenia with absent radii (TAR), radioulnar stenosis, familial platelet disorder with predisposition to acute myelocytic leukemia (FPD-AML), Platelet dense granule storage pool deficiency, grey platelet syndrome (also referred to as alpha granule deficiency), .alpha..delta.-storage pool deficiency, Bernard-Soulier Syndrome, Glanzmann Thrombasthenia, Scott Syndrome, Alport Syndrome, Quebec Syndrome, hermansky-Pudlack Disease, White Syndrome, and Wiskott-Aldrich Syndrome; platelet-associated disorders caused or affected by common drugs, including, but not limited to, aspirin (ASA), non-steroidal anti-inflammatory drugs (e.g., indomethacin, ibuprofen and naproxen), ticlopidine, antibiotics, heart drugs, blood thinners, antidepressants, anaesthetics, and antihistamines; and clotting and/or bleeding disorders or conditions associated with surgery, organ transplants, bone marrow transplants, chronic kidney disease, chemotherapy, and/or other medical procedures and/or treatments.

A platelet-associated disorder can include TLT-1-associated disorders, i.e., disorders, diseases or conditions which are caused, characterized by, related to, or associated with a misregulation (e.g., downregulation or upregulation) of TLT-1 expression and/or activity in any cell or tissue type in which TLT-1 may be expressed. Platelet-associated disorders can further detrimentally affect platelet-associated functions such as adhesion (e.g., via cell-cell and/or cell-matrix and/or basement membrane interactions), aggregation, secretion, procoagulant activity, and/or overall platelet number. For instance, in one example, the disease or disorder associated with platelet aggregation involves the interaction between platelets, e.g. platelet-platelet interaction. In another example, the disease or disorder associated with platelet aggregation involves the interaction between platelets and cells, e.g. platelet-cell interaction. In another related example, the disease or disorder associated with platelet aggregation involves the interaction between platelets and the endothelium, e.g. platelet-endothelial interaction. In one example, this interaction is an interaction between platelets and the cardiac endothelium. In exemplary embodiments, the above described platelet interactions are involved in the formation of a thrombus.

Cardiovascular Disease

A cardiovascular disease or disorder associated with platelet activity is suitable for treatment or diagnosis according to the methods and compositions of the invention. In preferred embodiments, a cardiovascular disease or disorder associated with platelet aggregation is suitable for treatment or diagnosis according to the methods and compositions of the invention.

Heart disease and stroke are the most common cardiovascular diseases. They are the first and third leading causes of death for both men and women in the United States, accounting for nearly 40% of all annual deaths. More than 910,000 Americans die of cardiovascular diseases each year, which is 1 death every 35 seconds. Although these largely preventable conditions are more common among people aged 65 or older, the number of sudden deaths from heart disease among people aged 15-34 has increased. In addition, more than 70 million Americans currently live with a cardiovascular disease. Coronary heart disease is a leading cause of premature, permanent disability in the U.S. workforce. Stroke alone accounts for disability among about 1 million Americans. More than 6 million hospitalizations each year are because of cardiovascular diseases. The economic impact of cardiovascular diseases on our nation's health care system continues to grow as the population ages. The cost of heart disease and stroke in the United States is projected to be $403 billion in 2006, including health care expenditures and lost productivity from death and disability. More information on cardiovascular disease in the United States can be found on the world wide web at cdc.gov.

Platelets play a life-saving role in hemostasis and blood clotting at sites of vascular injury; however as such platelets also play a crucial role in the development of arterial thrombosis and other pathophysiologies that lead to clinical ischemic events. Anti-platelet therapy has become a mainstay in treatment and/or prophylaxis of conditions like myocardial infarction, stroke and other cardiovascular diseases. Aspirin, acetyl-salicylic acid (ASA), is a widely used anti-platelet drug; however platelet activation occurs via several pathways that are not influenced by ASA. Thus, the methods of the instant invention may provide new ways to treat cardiovascular diseases and disorders that are associated with platelet aggregation.

Platelet adhesion to a damaged blood vessel is the initial trigger for arterial hemostasis and thrombosis. Platelets adhere to the subendothelium through an interaction with von Willebrand factor (VWF), which forms a bridge between collagen within the damaged vessel wall and the platelet receptor glycoprotein Ib/V/IX (GPIb) (35). This reversible adhesion allows platelets to roll over the damaged area, decreasing their velocity and resulting in strong platelet activation. This leads to the conformational activation of the platelet GPIIb/IIIa receptor, fibrinogen binding and finally to platelet aggregation. As each interaction (collagen-VWF, VWF-GPIb and GPIIb/IIIa-fibrinogen) plays an essential role in primary hemostasis, loss of either of these interactions results in a bleeding diathesis, implying that interfering with these interactions might result in an anti-thrombotic effect. Thus, the methods of the instant invention further find a use in inhibiting platelet adhesion. For example, the single chain TLT-1 antibody or function fragments or variants thereof, may be used to inhibit the initial steps of thrombus formation, and might have use in combination with therapies or agents, or other single chain antibodies, for example other single chain TLT-1 antibodies, that are directed at inhibiting platelet aggregation.

Studies have revealed that intimal thickening represents the first stage of atherosclerosis and that lipid-rich plaque arises from such lesions (39). Platelets release several growth factors and bioactive agents that play a central role in development of not only thrombus but also of intimal thickening, and thus methods and compositions of the invention may be useful in the atherosclerotic setting of inhibition of intimal thickening.

Inflammatory Diseases

An inflammatory disease or disorder associated with platelet activity is suitable for treatment or diagnosis according to the methods and compositions of this invention. In preferred embodiments, an inflammatory disease or disorder associated with platelet aggregation is suitable for treatment or diagnosis according to the methods and compositions of this invention.

When inflammation occurs, chemicals from the body's white blood cells are released into the blood or affected tissues in an attempt to rid the body of foreign substances. This release of chemicals increases the blood flow to the area and may result in redness and warmth. Some of the chemicals cause leakage of fluid into the tissues, resulting in swelling.

Activated platelets secrete a number of factors that may play a role in promoting the inflammatory response, both locally and at a distance. Some of these factors include platelet-derived growth factor, platelet factor 4, RANTES, thrombospondin, transforming growth factor-beta, nitric oxide, and CD-40 ligand.

In general, compositions and methods of the invention may be amenable to treatment of inflammatory diseases that are treated with non-steroidal anti-inflammatory drugs (NSAIDs).

The methods of the invention may be particularly useful for treating sepsis or septic shock. Recent work with the triggering receptor expressed in myeloid cells (TREM)-1 has shown that protein derivatives of the TREM-1 extracellular domain are effective in treating murine models of sepsis making TREM-1 a candidate drug target 1. Gibot et al. demonstrated that a 17 amino acid peptide derived from TREM-1 (LP17) was able to protect mice from both lipopolysaccharide (LPS) and cecal ligation-induced shock.

Multiple lines of evidence now suggest an important role for the Triggering Receptors Expressed on Myeloid cells (TREM) in the regulation of the septic response. TREM-Like Transcript (TLT)-1 is clustered with the TREM on chromosome 6 but has distinct biochemical characteristics and is expressed only on platelets and megakaryocytes. In specific examples of the invention, single chain, human Fv fragments that react with TLT-1 detect plate-bound TLT-1 fusion proteins, capture soluble TLT-1, and readily reacted with cell-bound TLT-1 on transfectants and primary human platelets. In an exemplary embodiment, anti-TLT scFv inhibits thrombin-mediated human platelet aggregation. This inhibition was specific for thrombin-induced aggregation, and was reversible with higher doses of agonist.

Taken together with studies of TREM-1 and -2 and two recent studies of TLT-1 Lu Y T, Yen C Y, Ho H C, Chen C J, Wu M F, Hsieh SL. Hybridoma (Larchmt) 2006 February; 25(1): 20-6; Gattis J L, Washington A V, Chisholm M M, Quigley L, Szyk A, McVicar D W, Lubkowski J. J Biol Chem 2006 Feb. 27), a model emerges where 4 independent genes within the TREM cluster, TLT-1, TLT-2, TREM-1, and TREM-2, may coordinate the physiologic response to sepsis. Whereas, TREM-1 and -2 regulate the cellular innate immune response to infection, TLT-1 could regulate the platelet-mediated thrombotic components of the response. This model predicts that intervention with TLT-1 may have significant impact, not only on diseases associated with sterile thrombosis, but in the management of sepsis and septic shock as well.

Cancer

The methods of the invention can be used to treat a disease or disorder associated with platelet activity, such as cancer. In preferred embodiments, the platelet activity is platelet aggregation.

In one particular aspect, the methods and compositions of the invention may be targeted to the tumor cell-platelet interaction. In the development of cancer, the formation of tumor cell-platelet aggregates facilitates hematogenous metastases, and thus instant invention may be useful in inhibiting this interaction. In another particular aspect, the methods and compositions of the invention may be useful in detecting occult cancer through the detection of thrombosis. For example, it has been reported that patients with venous thromboembolism have an increased risk for occult malignancy (40), thus the methods of the invention, in particular the methods to detect soluble TLT-1 or fragments thereof, may be useful in detecting occult cancers.

Methods of the Invention

In one aspect, the invention features a method of modulating platelet activity that comprises contacting cells with a single chain TLT-1 antibody or a functional fragment or variant thereof, to thereby modulate platelet activity.

In one aspect, the invention features a method of modulating platelet aggregation that comprises contacting cells with a single chain TLT-1 antibody or a functional fragment or variant thereof, to thereby modulate platelet aggregation.

As used herein a "platelet", also referred to as a "thrombocyte", refers to nucleus-free cytoplasmic fragments derived from large cells in the bone marrow, the megakaryocyte. Platelets play a crucial part in the blood clotting process by forming a platelet plug. This is a two-step process. First, single platelets bind to the site of the wound (adhesion). Next, the platelets bind to each other (activation). Activation can be stimulated by components released when the blood vessel is damaged and by thrombin, released during the blood clotting process. When platelets become activated they change, releasing agents that recruit and activate the surrounding platelets. The result of these two processes is the formation of fibrin which stabilizes the platelet plug, stops bleeding and allows injuries to heal. A platelet activity as used herein includes an activity which involves the action of platelets, including, but not limited to, platelet aggregation. Other platelet-mediated activities include adhesion to the site of a wound, activation (e.g., release of blood clotting factors), induction of blood clotting (e.g., induction of fibrin formation), inhibition of bleeding, and induction of wound healing. More specifically, platelet mediated activity may be regulated by factors that are secreted by the platelets, including platelet-derived growth factor, platelet factor 4, RANTES, thrombospondin, transforming growth factor-beta, nitric oxide, and CD-40 ligand.

Another aspect of the invention features a method wherein platelet activity is modulated in a subject. Platelet activity, in one example, is platelet aggregation. Further, the invention may feature a method of treating a disease or disorder associated with platelet aggregation in a subject, comprising administering to the subject a single chain anti-TLT-1 antibody or a functional fragment or variant thereof in an amount effective to modulate platelet aggregation, and thereby treating a disease or disorder associated with platelet aggregation. In another exemplary embodiment, the invention may feature a method of treating a subject at risk for a disease or disorder associated with platelet activity, comprising administering to the subject a single chain anti-TLT-1 antibody, or a functional fragment or variant thereof in an amount effective to modulate platelet activity, and thereby treating the disease or disorder associated with platelet activity. In exemplary embodiments, the disease or disorder is platelet aggregation. Determining if a patient is at risk for a disease or disorder can be done in any number of ways, including, but not limited to genetic testing, family history, and lifestyle or environmental risk factors.

In any of the methods of the invention, modulation can mean any alteration, an increase or a decrease, an inhibition or an activation, in a biological function or activity. Modulation can be a positive or negative change, measured in percent or fold change, for example 5%, 10%, 12%, 14%, 16%, 20%, 25%, 50% change, or 1.5-fold, 2-fold, 4-fold, 5-fold change. Thus, in exemplary embodiments, the invention features a method of inhibiting platelet aggregation with a single chain anti-TLT-1 antibody of a function fragment or variant thereof.

In any methods of the invention, a subject can be administered a single chain anti-TLT-1 antibody or a functional fragment thereof. The term "fragment" can refer to a portion of a protein or nucleic acid that is substantially identical to a reference protein or nucleic acid. For example, in some embodiments, the fragment is a fragment of a single chain anti-TLT-1 antibody. In some embodiments the portion retains at least 50%, 55%, 60%, 65%, 70%, 75%, 80%, 85%, 90%, 95%, 96%, 97%, 98%, or even 99% of the biological activity of the reference described herein. In other embodiments, the fragment comprises at least 5, 10, 11, 12, 13, 14, 15, 16, 17, 18, 19, or 20 amino acids of a reference single chain antiTLT-1 antibody.

In particular embodiments, platelet aggregation is mediated by thrombin. Generally, platelet aggregation refers to the clumping together of platelets in the blood. Platelet aggregation is part of the sequence of events leading to the formation of a thrombus, and as such platelets play a key role in hemostasis and thrombosis. The formation of a platelet plug is accompanied by the generation of thrombin, which results in the generation of fibrin required for stabilization of the platelet plug. Thrombin is a potent platelet activator, which proceeds through proteolysis of the protease activated receptors (PARs). Fibrinogen and fibrin, the end product of the coagulation cascade, are also involved in platelet aggregation.

The invention also features a method of diagnosing a subject with a disease or disorder associated with platelet activity, the method comprising detecting a soluble fragment of TLT-1 receptor, and thereby diagnosing the subject with a disease or disorder associated with platelet activity. The invention also features a method of diagnosing a subject with a disease or disorder associated with platelet aggregation, the method comprising detecting a soluble fragment of TLT-1 receptor, and thereby diagnosing the subject with a disease or disorder associated with platelet aggregation. In another aspect, the invention features a method of diagnosing a subject at risk for a disease or disorder associated with platelet aggregation, the method comprising administering to the subject a single chain TLT-1 antibody or a functional fragment or variant thereof in an amount effective to detect a soluble fragment of TLT-1 receptor, thereby diagnosing the subject at risk for a disease or disorder associated with platelet aggregation.

Another aspect of the invention features a method of diagnosing a subject as having, or having a propensity to develop, a disease or disorder associated with platelet activity, the method comprising determining the level of a soluble fragment of TLT-1 receptor in a subject, wherein a decreased level of soluble fragment relative to the level in a reference, indicates that the subject has or has a propensity to develop a disease or disorder associated with platelet activity. In exemplary embodiments, platelet activity is platelet aggregation.

In certain embodiments of the invention, it is useful to measure platelet aggregation. Platelet aggregation can be measured by the platelet aggregation test. Information on the platelet aggregation test can be found on the world wide web at nlm.nih.gov/medlineplus/ency/article/003669.htm. Accordingly, blood is drawn from the vein of a subject, from a site on the inside of the elbow or the back of the hand. The puncture site is cleaned with antiseptic, and an elastic band is placed around the upper arm to apply pressure and restrict blood flow through the vein. This causes veins below the band to swell with blood.

A needle is inserted into the vein, and the blood is collected in an airtight vial or a syringe. During the procedure, the band is removed to restore circulation. Once the blood has been collected, the needle is removed, and the puncture site is covered to stop any bleeding. For an infant or young child, the area is cleansed with antiseptic and punctured with a sharp needle or a lancet. The blood may be collected in a pipette (small glass tube), on a slide, onto a test strip, or into a small container. Cotton or a bandage may be applied to the puncture site if there is any continued bleeding.

The platelet aggregation test measures the rate and degree to which dispersed platelets in a sample of plasma (the liquid portion of blood) form clumps after the addition of a material that normally stimulates aggregation. These materials may include ADP (adenosine diphosphate), epinephrine, arachidonic acid, collagen, or ristocetin. Clumping of platelets causes the sample to be more clear (less turbid). A machine measures the changes in turbidity (cloudiness) and prints a graphic recording of the results.

Another method to measure platelet aggregation is using an aggregometry assay. The platelet aggregation assay is meant to detect or read an increase in transmission. Thus, if aggregation is inhibited, transmission will be inhibited. An alternative method to measure platelet aggregation is to measure absorbance, wherein the inhibition of platelet aggregation is measured by the lack of a decrease in absorbance. In a specific embodiment of the invention, the effects of single chain antibodies on platelets can be assessed using an aggregometry assay, wherein the scFvs are mixed with platelets before addition of thrombin, and then aggregation is measured using a commercially available chronology aggregometer.

A further method to measure platelet aggregation is a "microtiter plate assay." A microtiter plate assay provides a rapid, efficient and reproducible method for testing the function of modulators according to the instant invention. Microtiter plate assays are adaptable to high-throughput screening. An exemplary microtiter plate assay is described in the literature by Moran N. et al. (34), incorporated herein by reference in its entirety. The microtiter assay described can assay an average of 60 independent treatments per 60 ml blood donation and demonstrates high sensitivity, useful in the methods of the instant invention.

Other methods to measure platelet aggregation include commercially available aggregometers to easily assess of platelet aggregation, and clinical tests that measure platelet function include the template bleeding time and the platelet aggregation response to a standard set of platelet agonists as measured by platelet aggregrometry.

Any of the assays to measure modulation of platelet aggregation, including but not limited to the platelet aggregation assay, aggregrometry assay, and microtiter plate assay, can be performed on washed samples or whole blood. Washed platelets can be prepared after isolation, for example by centrifugation, by washing in a buffer solution. Exemplary buffer solutions according to the invention include Tyrode's solution (2 mM MgCl2, 137 mM NaCl, 2.68 mM KCl, 3 mM NaH2PO4, 0.1% glucose, 5 mM HEPES, and 0.35% albumin, pH 7.35) for use with human platelets, or modified mouse Tyrode's buffer (10 mM HEPES [N-2-hydroxyethylpiperazine-N'-2-ethanesulfonic acid], 138 mM NaCl, 5.5 mM glucose, 2.9 mM KCl, and 12 mM NaHCO3, pH 7.4).

Diagnostics

The presence of soluble TREM-1 in human serum has been shown to be a specific marker of bacterial infection (36), and TREM-1 expression patterns appear to correlate with survival of patients with sepsis (37). Moreover, the present inventors show that during platelet activation, there appears to be a time-dependent production of a soluble species of TLT-1, and the levels of this soluble TLT-1 species can be found in murine and human serum (22). Accordingly, the levels of a soluble species of TLT-1 in a subject are correlated with a particular disease state (e.g., cardiovascular diseases, inflammatory diseases, cancer), and thus are useful in diagnosis.

In certain embodiments, the present invention provides a method of diagnosing a subject as having, or having a propensity to develop, a disease or disorder associated with platelet activity. In preferred embodiments, the activity is platelet aggregation. The method comprises determining the level of a soluble fragment of TLT-1 receptor in a subject, where a decreased level of expression relative to the level of expression in a reference, indicates that the subject has or has a propensity to develop a disease or disorder associated with platelet activity, such as platelet aggregation.

In certain embodiments, the level of soluble fragment of TLT-1 receptor is determined using a single chain anti-TLT-1 antibody, or a functional fragment thereof, in an immunological assay.

Single chain anti-TLT-1 antibodies or functional fragments thereof are described herein and are used in the diagnostic methods of the invention.

Methods for measuring an antibody-TLT-1 complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra. Immunoassays can be used to determine the quantity of soluble TLT-1 or fragment thereof in a sample, where an decrease in the level of soluble TLT-1 or fragment thereof is diagnostic of a patient having a disease or disorder associated with platelet activity or aggregation.

In general, the measurement of a soluble fragment of TLT-1 receptor in a subject sample is compared with a diagnostic amount present in a reference. A diagnostic amount distinguishes between a subject having a disease or disorder, or a subject having a propensity to develop a disease or disorder, and a control subject. The sample is a biological sample. In exemplary embodiments, the sample is independent platelets. In other embodiments, the sample is whole blood. The skilled artisan appreciates that the particular diagnostic amount used can be adjusted to increase sensitivity or specificity of the diagnostic assay depending on the preference of the diagnostician. In general, any significant decrease (e.g., at least about 10%, 15%, 30%, 50%, 60%, 75%, 80%, or 90%) in the level of a soluble fragment of TLT-1 receptor in a subject sample relative to a reference may be used to diagnose a disease or disorder associated with platelet aggregation. In one embodiment, the reference is the level of soluble fragment of TLT-1 receptor present in a control sample obtained from a patient that does not have a disease or disorder associated with platelet aggregation. In another embodiment, the reference is a baseline level of soluble fragment of TLT-1 receptor present in a biologic sample derived from a patient prior to, during, or after treatment for a disease or disorder associated with platelet aggregation. In yet another embodiment, the reference is a standardized curve.

Types of Samples

Platelet activity, for example platelet aggregation, can be modulated in different types of samples. Likewise, soluble fragment of TLT-1 receptor can be measured in different types of samples. Generally, samples that are suitable for use according to the methods of the invention are biological samples containing platelets. In one embodiment, the sample is independent platelets. In another embodiment, the sample is whole blood.

Pharmaceutical Compositions

The present invention encompasses pharmaceutical compositions and immunogenic compositions containing TLT-1 antibody or a functional fragment or variant thereof, either alone or in combination. Such pharmaceutical compositions are useful for eliciting an immune response and treating a disease or disorder associated with platelet aggregation, either alone or in conjunction with other forms of therapy, such as anticoagulant therapies, anti-inflammatory therapies, chemotherapeutics, cardiovascular therapies.

Anticoagulant therapy refers to the use of certain drugs to prevent formation of harmful blood clots. Individuals at high risk for thromboembolic events (thrombosis and embolism) are potential candidates for receiving anticoagulant therapy, including surgery patients, dialysis patients and bedridden patients. In general, anticoagulant therapies can be categorized in to three classes: Clotting Factor inhibitors (e.g. Warfarin), Thrombin inhibitors (e.g. Heparin, Lepirudin) and Platelet Inhibitors (e.g. aspirin, Eptifibatide, Tirofiban, Clopidogrel, Ticlopidine).

A variety of anti-inflammatory agents are known in the art. According to the present invention, a suitable anti-inflammatory agent may be used to treat a disease or disorder associated with platelet aggregation. Non steroidal anti-inflammatory drugs (NSAIDs) are an exemplary class of anti-inflammatory agents. NSAIDs include aspirin and aspirin-like compounds that are generally used to treat pain, inflammation, and fever. They inhibit the function of enzymes involved in the immune system's inflammatory response. NSAIDs include non-selective and selective NSAIDs. Selective NSAIDs include COX-2 selective NSAIDs. NSAIDs are sold in over-the-counter and prescription dosages. Other agents particularly useful in the invention are agents that target the TREM receptors, in particular, but not limited to TREM-1.

A wide variety of chemotherapeutics are known in the art and may be used in combination therapies in the practice of the invention. Chemotherapeutic agents contemplated by the present invention include chemotherapeutic drugs that are commercially available.

Merely to illustrate, the chemotherapeutic can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas exotoxin, Bordetella pertussis* adenylate cyclase toxin, or diphtheria toxin, and caspase activators; and chromatin disruptors. Preferred dosages of the chemotherapeutic agents are consistent with currently prescribed dosages.

Cardiovascular therapies that can be used in combination with the methods and compositions of the invention include treatment with an agent, or surgical intervention. Treatment with an agent includes treatment for any cardiovascular disease or disorder, such as stroke, heart disease, atherosclerosis, or any other cardiovascular disorder associated with platelet aggregation.

In another embodiment of the invention, the TLT-1 antibody compositions may be administered to a patient before or during a surgical procedure, for example, a patient undergoing a coronary stent procedure. Administration of the TLT-1 antibody compositions are especially beneficial to a patient who has been determined to be of a high risk, for example a patient who has suffered a prior coronary event or who has a family history of coronary events.

The preparation of pharmaceutical compositions that contain TLT-1 antibody or a functional fragment or variant thereof, or a polynucleotide or a polypeptide derivative thereof, as an active ingredient is conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the active ingredient further in the preparation of pharmaceutical compositions. The TLT-1 antibodies (also referred to herein as "active compounds") of the invention can be incorporated into pharmaceutical compositions suitable for administration. Such compositions typically comprise the antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions Appropriate processing may include sterilizing, mixing with appropriate non-toxic and non-interfering components, dividing into dose units, and enclosing in a delivery device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

Pharmaceutical compositions of the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions of this invention for human use are typically administered by a parenteral route, most typically intracutaneous, subcutaneous, or intramuscular.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby a relatively consistent level of the active compound are provided over an extended period. Therapeutic compositions of TLT-1 antibody can be administered by injection or by gradual perfusion.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It may be desirable to administer the compositions locally to the area in need of treatment; this can be achieved by, for example, local infusion during surgery, by injection, by means of a catheter, or by means of an implant, said implant being of a porous, non-porous, or gelatinous material, including membranes, such as silastic membranes, or fibers. A suitable such membrane is GLIADEL®, provided by Guilford Pharmaceuticals Inc.

Compositions embodied in this invention can be assessed for their ability to modulate platelet aggregation. Accordingly, test compounds are prepared as a suitable pharmaceutical composition and administered to test subjects. Initial studies are preferably done in small animals such as mice or rabbits, optionally next in non-human primates and then ultimately in humans. Immunogenicity is preferably tested in individuals without a previous antibody response. A test composition in an appropriate dose is administered on an appropriate treatment schedule. It may be appropriate to compare different doses and schedules within the predicted range. Such testing is within the skill of one in the art.

Compositions of this invention are particularly suitable for administration to subjects with disease or disorder associated with platelet aggregation. Especially relevant are cardiovascular disease, thrombosis, heart attack, stroke, sepsis, septic shock, and cancer.

The dosage ranges for the administration of TLT-1 antibody or a functional fragment or variant thereof, are those large enough to produce the desired effect in which the symptoms of the disease or disorder associated with platelet aggregation are ameliorated without causing undue side effects such as unwanted cross-reactions, anaphylactic reactions, and the like. Generally, the dosage will vary with the patient's age, condition, sex and extent of the disease and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg in one or more dose administrations daily, for one or several days. Generally, when TLT-1 antibodies are administered conjugated with therapeutic agents, lower dosages can be used.

Subjects, including those who are suspected of being at risk of a disease or disorder associated with platelet aggregation, are suitable for treatment with the pharmaceutical compositions of this invention. Those with a history, or a family history, of cardiovascular disease, including but not limited to thrombosis, heart attack, or stroke, or inflammatory diseases, for example, sepsis, septic shock, or cancer, are especially suitable. Suitable subjects for treatment comprise those with a disease or disorder associated with platelet aggregation as described herein. A pharmaceutical composition embodied in this invention is administered to these patients to elicit a response to modulate platelet aggregation, with the objective of palliating their condition. Ideally, to modulation of platelet aggregation occurs as a result, in preferred embodiments, the modulation is an inhibition, but any clinical improvement constitutes a benefit. Clinical improvement includes decreased risk or rate of progression or reduction in pathological consequences of the disease or disorder.

A pharmaceutical composition embodied in this invention is also suitable for coating a device. For example, a pharmaceutical composition according to the invention may be used to coat a device for implantation in to a patient, e.g. coating of a stent for implantation in to a heart surgery patient. In certain embodiments, coating a medical device with the composition of the invention may be a desirable route for administration to maintain the necessary concentration of a therapeutic substance at the lesion site for the necessary period of time. For example, coating a stent with a TLT-1 antibody composition according to the instant invention can provide local delivery of a therapeutic substance from the stent itself. Being made of metal, plain stents are not useful for therapeutic substance delivery. Therefore, a coating, usually made from a polymer, is applied to serve as a therapeutic substance reservoir. A solution of a polymer dissolved in a solvent and a therapeutic substance added thereto is applied to the stent and the solvent is allowed to evaporate. Accordingly, a polymeric coating impregnated with a therapeutic substance remains on the surface of the stent. The polymeric coating can include multiple layers. A primer composition, free from any drugs, can be applied on the surface of the device. A polymer solution including the agent or drug can then be applied on the primer layer. To reduce the rate of release of the agent or drug, a topcoat layer can be applied over the reservoir layer. The application of each layer can be performed subsequent to the drying of the previous layer. Methods of coating implantable medical devices are well-known in the art, and are described in, for example U.S. Pat. No. 7,115,300, incorporated by reference herein in its entirety.

Various compounds and compositions of this invention have other clinical indications. For example, cells may be treated ex vivo. This may be desirable for experimental purposes, or for treatment of an individual with a disease or disorder associated with platelet aggregation. In one example donor cells are genetically altered with an expression vector of this invention, to provide for ongoing secretion of TLT-1 antibody after administration of the cells to the recipient.

Antibody Targeted Gene Therapy

Also encompassed by the invention are expression systems suitable for use in antibody-targeted gene therapy comprising single chain TLT-1 antibody or a functional fragment or variant thereof. Suitable systems are described for instance by Brown et al. (1994) Virol. 198:477 488; and Miyamura et al. (1994) Proc. Natl. Acad. Sci. USA 91:8507 8511.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus, which is discussed below). The choice of introducing vectors will often depend on features of the host cell.

Once introduced into a suitable host cell, expression of the single chain TLT-1 antibody or a functional fragment or variant thereof can be determined using any assay known in the art. For example, presence of TLT-1 antibody or a functional fragment or variant thereof polypeptide can be detected by RIA or ELISA of the culture supernatant or cell lysates.

A vector of this invention can contain one or more polynucleotides encoding TLT-1 antibody or a functional fragment or variant thereof. It can also contain polynucleotide sequences encoding other polypeptides that enhance, facilitate, or modulate the desired result, such as lymphokines, including, but not limited to, Interleukin-2 (IL-2), Interleukin-4 (IL-4), Granulocyte macrophage colony-stimulating factor (GM-CSF), tumor necrosis factor-alpha (TNF-α), and interferon-gamma (IFN-γ). A preferred lymphokine is GM-CSF. Preferred GM-CSF constructs are those which have been deleted for the AU-rich elements from the 3' untranslated regions and sequences in the 5' untranslated region that are capable of forming a hairpin loop. Also embodied in this invention are vaccinia vectors encoding for recombinant single chain TLT-1 antibody variants, such as chimeras, and polymers.

Other embodiments of this invention are host cells transformed with single chain anti-TLT-1 antibody or a functional fragment or variants thereof, and vectors comprising single chain anti-TLT-1 antibody or a functional fragment or variant thereof, as described above. Both prokaryotic and eukaryotic host cells may be used. Prokaryotic hosts include bacterial cells, for example *E. coli* and *Mycobacteria*. Among eukaryotic hosts are yeast, insect, avian, plant and mammalian cells. Host systems are known in the art and need not be described in detail herein. Examples of mammalian host cells include Chinese hamster ovary (CHO) cells, obtainable from the ATCC. Transfection of NSO cells with a plasmid, for example, which is driven by a cytomegalovirus (CMV) promoter, followed by amplification of this plasmid in using glutamine synthetase provides a useful system for protein production. Cockett et al. (1990) Bio/Technology 8:662 667.

The host cells of this invention can be used, inter alia, as repositories of single chain anti-TLT-1 antibody or a functional fragment or variant thereof, or as vehicles for production of anti-TLT-1 antibody or a functional fragment or variant thereof. They may also be used as vehicles for in vivo expression of TLT-1 antibody or a functional fragment or variant thereof.

Combination Therapies

In certain embodiments of the invention, the methods are performed in combination with other therapies. For example, the subject is administered a single chain anti-TLT-1 antibody or a functional fragment or variant thereof in an amount effective to modulating platelet aggregation, and is also undergoing an additional therapy. The combination therapy of the single chain anti-TLT-1 antibody and additional therapy may take place at the same time, e.g. co-administration, or may take place at different times. For example, the subject may have previously received the additional therapy prior to receiving the single chain anti-TLT-1 antibody; alternatively, the subject may first receive the single chain anti-TLT-1 antibody, and then receive the additional therapy.

Additional therapies include any therapy that is useful for the treatment of the following conditions: immune disorders, disseminated intravascular coagulation, acute respiratory syndrome, atherosclerosis, sepsis, septic shock, cancer (e.g., leukemias such as acute megakaryocytic leukemia, megakaryoblastic leukemia), infectious disease, stroke, heart disease, myocardial infarction, vascular disorders, arteriosclerosis, clotting and/or bleeding disorders, platelet insufficiency, TLT-1 associated disorders, Hemophilia A (Factor VIII deficiency), Hemophilia B (Factor IX deficiency), von Willebrand disease, beta.-thalassemia, deep-vein thrombosis, thrombocytopenia, Immune Thrombocytopenic Purpura, Idiopathic Thrombocytopenic Purpura, Thrombotic Thrombocytopenic Purpura, hypercoagulation, hypocoagulation, protein S deficiency, protein C deficiency, Factor V Leiden, thrombosis, superficial vein thrombosis, phlebitis, thrombophlebitis, Factor XI deficiency (Rosenthal Syndrome or Plasma Thromboplastin Antecedent (PTA) deficiency), Factor XII deficiency (Hageman factor deficiency), Vitamin K deficiency, generalized coagulopathy, Factor XIII deficiency, Factor VII deficiency, internal bleeding, gastrointestinal bleeding, intracranial bleeding, pulmonary embolism, Afibrinogenemia, Dysfibrinogenemia, Factor II disorders, Factor III (tissue factor) associated disorders, Factor V (labile factor) deficiency, Factor X deficiency, Factor V & VIII Combined Deficiency, Factor VIII & IX combined Deficiency, Factor IX & XI Combined Deficiency, Thrombophilia (Antithrombin III deficiency), Giant Platelet Syndrome (platelet glycoprotein Ib deficiency), Fletcher Factor Deficiency (Prekallikrein deficiency), Autosomal dominant macrothrombocytopenia, the May-Hegglin anomaly, Sebastian syndrome, Fechtner syndrome, platelet storage pool deficiency, Chediak-Higashi syndrome, amegakaryocytic thrombocytopenia, thrombocytopenia with absent radii (TAR), radioulnar stenosis, familial platelet disorder with predisposition to acute myelocytic leukemia (FPD-AML), Platelet dense granule storage pool deficiency, grey platelet syndrome (also referred to as alpha granule deficiency), .alpha..delta.-storage pool deficiency, Bernard-Soulier Syndrome, Glanzmann Thrombasthenia, Scott Syndrome, Alport Syndrome, Quebec Syndrome, White Syndrome, and Wiskott-Aldrich Syndrome; platelet-associated disorders caused or affected by common drugs, including, but not limited to, aspirin (ASA), non-steroidal anti-inflammatory drugs (e.g., indomethacin, ibuprofen and naproxen), ticlopidine, antibiotics, heart drugs, blood thinners, antidepressants, anaesthetics, and antihistamines; and clotting and/or bleeding disorders or conditions associated with surgery, organ transplants, bone marrow transplants, chronic kidney disease, chemotherapy, and/or other medical procedures and/or treatments.

The dosage ranges for the administration of anti-TLT-1 antibody or a functional fragment or variant thereof and an additional agent are those large enough to produce the desired effect in which the symptoms of the disease or disorder associated with platelet aggregation are ameliorated without causing undue side effects. Generally, the dosage will vary with the patient's age, condition, sex and extent of the disease and can be determined by one of skill in the art. The dosage can be adjusted by the individual physician in the event of any complication. Generally, when TLT-1 antibodies are administered in addition with other therapeutic agents, lower dosages can be used.

Kits

The present invention encompasses kits containing a single chain anti-TLT-1 antibody or a functional fragment or variant thereof, and instructions for use. In specific examples, the kit comprises a single chain anti-TLT-1 antibody or a functional fragment or variant thereof in an amount effective to modulate platelet aggregation, and instructions for use.

The kits encompassed by the invention can be used in treating a disease or disorder associated with platelet aggregation in a subject. The kits encompassed by the invention can also be used in modulating platelet aggregation in a subject at risk for a disease or disorder associated with platelet aggregation. The kits encompassed by the invention can further be used in treating a subject at risk for a disease or disorder associated with platelet aggregation. The kits encompassed by the invention can be used in treating a subject that is currently or previously being treated for a disease or disorder associated with platelet aggregation.

The kits encompassed by the invention comprise a single chain anti-TLT-1 antibody or a functional fragment or variant thereof in an amount effective to modulating platelet aggregation. In certain embodiments, the modulation is an inhibition of platelet aggregation. The kits can contain an additional therapeutic agents, and instructions for use. Exemplary therapeutic agents include those that are used in the treatment of disease or disorder associated with platelet aggregation. For example, cardiovascular disorders, inflammatory disorders, immune disorders, cancers (e.g., leukemias such as acute megakaryocytic leukemia, megakaryoblastic leukemia), infectious disease, stroke, heart disease, myocardial infarction, vascular disorders, arteriosclerosis, clotting and/or bleeding disorders, platelet insufficiency, and TLT-1 associated disorders, and other diseases and disorders as described herein.

Other kits encompassed by the methods of the invention include kits used for determining the level of a soluble fragment of TLT-1 receptor in a subject. The kits comprise a single chain anti-TLT-1 antibody or a functional fragment thereof in an amount effective to detect the level of soluble TLT-1 receptor or fragment in a subject. These kits are particularly useful in diagnostic methods.

This invention is further illustrated by the following examples, which should not be construed as limiting. All documents mentioned herein are incorporated herein by reference.

EXAMPLES

The invention will now be further described by way of the following non-limiting examples. Considered first are the materials and methods which were used in the examples.

Materials and Methods of the Invention

The results reported herein were obtained using the following Materials and Methods:

Antibody Library and Bacterial Strains

The Human Single Fold scFv library Tomlinson I used was acquired from the Medical Research Council Geneservices, Cambridge, United Kingdom (reference found on the world wide web at geneservice.co.uk/products/proteomic/scFv_tomlinsonIJ.jsp). The library was amplified as previously described in the literature (Goletz S, Christensen P A, Kristensen P, Blohm D, Tomlinson I, Winter G, Karsten U. Selection of large diversities of antiidiotypic antibody fragments by phage display. J Mol Biol 2002; 315:1087-97). Helper phage KM13 and Escherichia coli HB2151 were also provided by MRC. E. coli TG1 was purchased from Stratagene (La Jolla, Calif.).

Panning of the Library

Panning of the library was performed in immunotubes (Maxisorp, Nunc, Gaithersburg, Md.) as previously described (18). Briefly, tubes were coated with a purified TLT-1/Fc fragment fusion protein (TLT-1-Fc) (10) (10 μg/ml for the first and second round, and 1 μg/ml for the third round) or with Fc fragment (Bethyl, Montgomery, Tex., 100 μg/ml) in phosphate buffer saline (PBS), washed with PBS, and blocked with 2% skimmed milk in PBS (MPBS). All incubations of phages in immunotubes were at room temperature (RT) for 2 hrs in a total volume of 1 ml. A subtraction step was used to deplete the members of library that bind to the Fc fragment part of TLT-1-Fc. Phages (approximately 2×1012 transducing units, TU) were incubated with 2% MPBS in immunotubes coated with Fc fragment. The subtracted library was then incubated in immunotubes coated with TLT-1-Fc. Fc fragment (10 μg/ml) was also added to the solution during the selection to further remove the library members that reacted with Fc. Unbound phages were removed by washing at least ten times with PBS+0.1% Tween 20 (PBS-T). Bound phages were eluted by trypsin (Sigma, Saint Louis, Mo.) and rescued by reinfection of E. coli TG1 as previously described (18). Rescued phages were used for the next round of selection. Three rounds of selection were carried out.

Selection of Anti-TLT-1 Phage Clones

Individual clones were randomly picked out from the phage pools of three rounds of selection. Phages were produced and used for monoclonal phage ELISA as previously described (19). Briefly, 96-well plates (Maxisorp Nunc-Immunoplates, Nunc) were coated with TLT-1-Fc (100 ng/well in PBS) or with Fc fragment (1 μg/well) and blocked with MPBS. A control plate was incubated with MPBS only. The supernatants containing scFv-phages were incubated in the TLT-1-Fc-coated plate and in the control plates. Phage binding was detected with HRP-conjugated anti-M13 antibody (Amersham Bioscience, Piscataway, N.J.).

Sequencing of the Selected Clones

The scFv insert of individual clones was amplified using a high-fidelity polymerase Pfu (Platinum PCR Supermix, Invitrogen) with the following primers:

```
LMB3        (5'-CAGGAAACAGCTATGAC-3')
and pHENseq     (5'-CTATGCGGCCCCATTCA-3')
```

Primers used for sequencing of the PCR products were:

```
Link-seq-new  (5'-CGACCCGCCACCGCCGCTG-3')
and pHENseq       (5'-CTATGCGGCCCCATTCA-3')
```

Expression and Purification of Soluble scFvs

Production of soluble scFvs was performed in the non-suppressor E. coli strain HB2151 as previously described (19, 20). Expression of scFvs was induced by adding 1 mM isopropyl-β-D-thiogalactopyranoside (IPTG) when the optical density at 600 nm (OD600) of the HB2151 cultures was 0.9 and growing with shaking (250 rpm) for 16 hrs at 30 C. Supernatants were subjected to SDS-PAGE in a Tris-glycine 8-16% gel and proteins were transferred to a polyvinylidene difluoride (PVDF) membrane according to standard procedures. The membrane was blocked with 3% MPBS and probed with HRP conjugated anti-pentahistidine (His-tag) (SEQ ID NO: 10) antibody (Qiagen, Hilden, Germany). For purification of scFvs, supernatants were filtered through a 0.2 μm-pore size membrane (Corning, N.Y.) and subjected to ammonium sulfate precipitation at 70% saturation (4 C). The resulting precipitates were dissolved and dialyzed in PBS. scFvs were purified by Protein L columns (Pierce, Rockford, Ill.) according to manufacturer's instructions. Purified scFvs were dialyzed in PBS at 4° C. for 16 hrs. Purity of the scFvs was evaluated by SDS-PAGE.

Cell Culture and Transfection

Human embryonic kidney (HEK)293T cells were maintained and transfected as previously described (21). Human TLT-1 cDNA was generated by RT-PCR using Platinum HiFi-Supermix (Gibco-BRL, Grand Island, N.Y.) with human platelet cDNA as a template and cloned into pEF6V5-His TOPO (Invitrogen) using primers: forward (5'-ATGGGCCT-CACCCTGCTCTTG-3') (SEQ ID NO: 11) and reverse (5'-GCTGGATGGAGTCTGATTG-3'). (SEQ ID NO: 12). Human venous endothelial cells were kindly provided by Giovanni Melillo (NCI Frederick). Cell purifications were completed as previously described (10).

Preparation of Platelets

Fresh platelets concentrated in acid-citrate-dextrose was obtained from the NIH blood bank. Washed platelets were prepared as previously described (22). To prepare platelet-rich plasma (PRP), whole blood was collected in acid citrate dextrose (1:7) from healthy volunteers and centrifuged at 800×g to for 20 min to remove red blood cells. Half of the collected PRP was spun at 2,100×g to remove platelets, and the resulted platelet-poor plasma was used to dilute the PRP to $3.2 \times 10^8$ platelets/ml with the addition of Ca2+ (2 mM) and aparase (0.02 units, U/ml). Platelets were isolated by centrifugation at 2,100×g for 10 min and resuspended in Tyrode's solution (2 mM MgCl2, 137 mM NaCl, 2.68 mM KCl, 3 mM NaH2PO4, 0.1% glucose, 5 mM HEPES, pH 7.35) at a final concentration of $3.2 \times 10^8$ cells/ml. Ca2+ and aparase were added at final concentration of 2 mM and 0.02 U/ml, respectively.

Flow Cytometry

For flow cytometric analysis with TLT-1-transfected cells, phage-containing supernatants were prepared from individual colonies as previously described (14). (HEK)293T-TLT-1 transfected cells ($2 \times 10^5$ cells) were washed with PBS/1% BSA and incubated with phages ($2 \times 10^{10}$ TU) or purified scFv (1 μg/ml). After 1 hr of incubation at 4° C., cells were washed twice with PBS/1% BSA. Phage binding was detected by incubation with mouse anti-M13 monoclonal antibody (Amersham Bioscience, Piscataway, N.J.), followed by incubation with phycoerithrin (PE)-conjugated anti-mouse antibody (Jackson Immunoresearch, West Grove, Pa.). To analyze scFv binding to human platelets, platelets were incubated with 1 μg of purified scFv for 1 hour at 4° C. and washed three times with PBS containing 0.5% sodium azide and 0.5% BSA. ScFv binding was detected using a FITC-conjugated anti-c-myc antibody (Sigma, St Louis, Mo.). TLT-1 expression was detected with a commercial anti-human TLT-1 pAb (R&D Systems, MN) as previously described (10).

Platelet Aggregation

Aggregation assay was run on a chronology aggregrometer (Chronolog, Havertown, Pa.). ScFvs or vehicle (PBS) were added and allowed to incubate with the PRP or with washed platelets for 3 min at 37 C with stirring (800 rpm) before adding the agonists. Thrombin (0.125 U), collagen (5 μg/ml), or phorbol myristate acetate (PMA, 10 nM) was added to the aggregation cuvette containing 600 μl of platelet suspension ($3 \times 10^9$/ml), and results were recorded by a chart recorder for at least 5 minutes.

Immunoprecipitation

For immunoprecipitation (IP), platelets ($3 \times 10^8$/ml) in tyrodes buffer, containing 13 mM ethylene glycol-bis(b-aminoethyl ether)-N,N,N',N'-tetraacetic acid (EGTA) were incubated with or without thrombin (1 U/ml). Cells were lysed as previously described (10), and 2 μg of purified scFv was incubated with the whole cell lysate in a volume of 1 ml with rotation at 4 C overnight. Fifty μl of Protein L beads, which were washed 3 times with PBS, were added per ml of lysate, and washed 3 times with 0.1% triton X-100 after rotating for 1 hr at 4 C. Proteins were eluded from the beads by boiling in SDS sample buffer. For immunoblotting eluted proteins were resolved by SDS-PAGE on 7% acrylamide gels. Immunoblotting was performed by transferring the proteins to a PVDF membrane and probing with anti-human TLT-1 pAb (R&D Systems, MN). Bound antibodies were detected using HRP-conjugated goat anti-rabbit IgG (Amersham Biosciences, Buckinghamshire, UK).

Example 1

Expression and Characterization of hTLT-1

Figure 1:
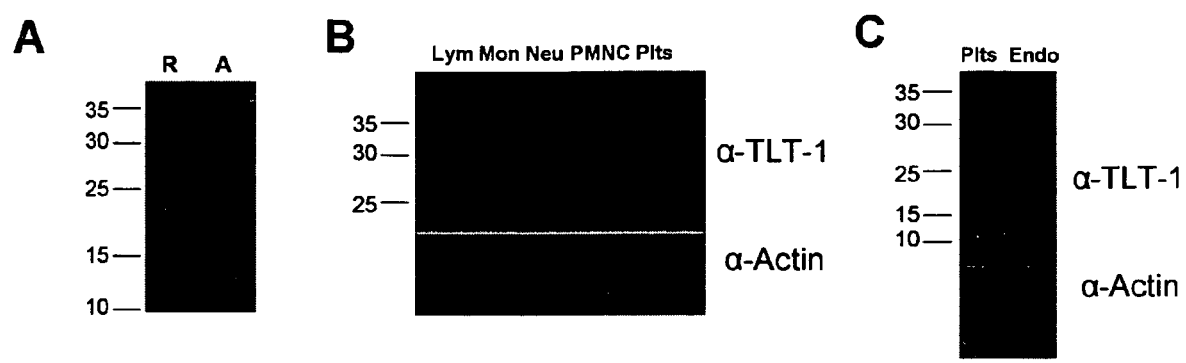
FIG. 1 (A-C) are Western blots that show TLT-1 expression in the peripheral blood. Panel A shows expression of TLT-1 in human platelets. Western blot analysis of TLT-1 expression was performed using 10 μg of resting (R) or activated (A) platelets. A commercial anti-TLT-1 polyclonal antibody (pAb) was used for TLT-1 detection. Panel B is a Western blot showing that TLT-1 is only expressed in platelets. Peripheral blood populations were separated, and whole cell lysate (WCL) of $2\times10^6$ cells were analyzed by Western blot for TLT-1 expression probing with anti-TLT-1 pAb. Panel C is a Western blot that shows TLT-1 is not expressed in endothelial cell lines. Western blot using human venous endothelial cells (Endo) and platelets (plts) and WCL probed with anti-TLT-1 pAb.

It has previously been shown that murine TLT-1 (mTLT-1), which has an expected molecular weight of 34 kDa, is expressed as a 45 kDa-protein in peripheral blood platelets, likely due to glycosolation (10). To analyze the expression of various human TLT-1 (hTLT-1) isoforms in the peripheral blood and in different cell types a goat anti-hTLT-1 polyclonal antibody (pAb) was used to probe whole cell lysate of resting or thrombin-activated platelets in western blot analysis. The results are shown in FIG. 1A. Two major bands of 35 and 25 kDa were detected in both resting and activated platelets. The 25 kDa band corresponds to the TLT-1 sp reported by Barrow et al. (2004), and as further suggested by comparison of these results with western blot analysis of transfected hTLT-1 cDNAs (22). A minor band of 33 kDa was also detected in both resting and activated platelets, while three bands of 15, 13 and 11 kDa were visible in resting but not in activated platelets. These low molecular weight bands correspond to degradation products or alternative transcripts of TLT-1 (22). In the mouse, TLT-1 is only found in megakaryocytes and platelets (Washington, 2004). Previous northern analysis data on human peripheral blood subsets suggested that hTLT-1 might also be platelet specific (10). To evaluate this at protein level, lymphocytes, monocytes, neutrophils, polymorphonucleate cells (PBMCs), human vascular endothelial cells (HUVECs), and platelets were isolated and probed with the anti-TLT-1 pAb in western blot analysis, as shown in FIGS. 1B and 1C). TLT-1 was detected only in platelets, thus confirming that TLT-1 expression in the peripheral blood compartment in humans, as in mice, is specific for platelets.

Example 2

Isolation and Characterization of Monoclonal Phage Antibodies Specific for TLT-1

With the aim of defining the role of TLT-1 in platelets and broadly screen for antibodies to potentially functional epitopes, next, human scFvs specific for TLT-1 were isolated from a naïve library of phage-displayed scFvs. A repertoire of $1.47 \times 10^8$ antibody clones was panned against a fusion of the extracellular domain of TLT-1 with the Fc fragment of human IgG$_1$ (TLT-1-Fc). Three rounds of panning resulted in significant enrichment of phage that bound specifically to TLT-1, as assessed by ELISA, whereas no significant binding was detected with pooled phage from any of the rounds when TLT-1-Fc was replaced with the human Fc fragment alone (data not shown). A total of 180 clones were randomly picked from the phage pools from each round of selection and 57 clones with the highest reactivity against TLT-1-Fc, and no reactivity against human Fc were selected in a phage ELISA and subjected to further characterization. A representative phage ELISA for six selected clones is shown in FIG. 2A. To verify that the clones bound to TLT-1 in its native conformation, phage-containing supernatants were analyzed by flow cytometric analysis on (HEK)293T cells transfected with TLT-1. The vast majority of phage clones (96%) bound to TLT-1 expressing cells, as represented for clone C10 (FIG. 2B, indicated with arrow, and FIG. 2C, upper panel). No binding was detected for the naïve library (FIG. 2B, neg. control) or when clones were screened against control cells that do not express TLT-1 (FIG. 2C, bottom panel). The analysis of the deduced amino acid sequences of $V_H$ and $V_L$ revealed the presence of 24 different clones (data not shown). The complementary determining regions (CDR)1 and the framework regions of all clones were identical (data not shown). The CDR2 and CDR3 of $V_H$ and $V_L$ domains were the same length in all clones and showed partial sequence variability. Table 1, below, shows the deduced amino acid sequences of CDR2 and CDR3 of $V_H$ and $V_L$ domains of the selected scFvs. Identical residues are denoted by (-). CDRs were identified based on Kabat definition (found on the world wide web at bioinf.org.uk/abs/). The complete DNA sequences of these scFvs are available at GenBank (accession numbers DQ375449 to DQ375454). The specificity of binding to TLT-1 for the selected clones was further confirmed by a phage ELISA with other immobilized antigens and they showed a lack of reactivity to BSA, ubiquitin, and mouse activating receptor 1 (MAR-1), a receptor with homology to TREMs and TLT-1 (data not shown). MAR-1 was a gift from Dr. John Ortaldo (NCI-Frederick). Taken together, this data shows isolation and characterization of monoclonal phage antibodies specific for TLT-1.

TABLE 1

(VH-CRD2, VH-CRD3, VL-CDR2 and VL-CDR-3 sequences disclosed as SEQ ID NOS 13-36, respectively, in order or appearance)

| Clone | VH-CDR2 | VH-CDR3 | VL-CDR2 | VL-CDR3 |
| --- | --- | --- | --- | --- |
| A1 | GIGTTGYATAYADSVKG | GNSGFDY | TASTLQS | QQSSTDPGT |
| A7 | A-GSY-SA-A------- | NGYD--- | N--G--- | --SAAN-S- |
| A8 | G-GTT-YS-A------- | TAYT--- | S--T--- | --NSTY-A- |
| B8 | N-TAS-YA-A------- | TTAT--- | D--N--- | --DTAS--S |
| C10 | G-SST-GA-T------- | STYD--- | G--T--- | --NADA-T- |
| D1 | A-GTT-YA-A------- | ANSY--- | S--T--- | --DSTS-D- |

Example 3

Production and Characterization of Soluble scFvs

Selected phage clones were used to infect *E. coli* HB2151 to produce soluble scFvs. Based on the highest binding activity of the scFvs to TLT-1-Fc immobilized in an ELISA assay, six clones (designated A1, A7, A8, B8, C10, and D1) were selected for purification and further characterization (FIG. 2A). The bacterial supernatants were concentrated by ammonium sulfate precipitation and subjected to purification in protein L columns. Purity of the scFvs was judged by coomassie staining on SDS-PAGE, as shown in FIG. 3A, left panel, and FIG. 3B. The purified scFvs reacted on Western blot with an anti-His antibody-HRP conjugate and showed a single band of the expected molecular weight (28 kDa) as shown for scFv C10 in FIG. 3A (right panel). Binding of the purified scFvs to immobilized TLT-1-Fc in ELISA was demonstrated, as shown in FIG. 3C. The binding activity of scFvs was also detected by antigen-capture ELISA, immobilizing the scFvs on a plate and incubating with different amounts of TLT-1-Fc in solution. TLT-1-Fc binding was then detected using an anti-TLT-1 pAb (FIG. 3D). Using this method the scFv with the highest capture activity for TLT-1-Fc was C10 and as little as 3 ng/well of the purified protein was detectable (data not shown). To confirm the specificity of the scFvs, binding activity to TLT-1 transfected cells was demonstrated in flow cytometric analysis (data not shown).

Example 4

Binding of the Anti-TLT-1 scFvs to Platelets

To test the binding activity of the selected scFvs to TLT-1 in the context of the platelet surface, flow cytometric analysis was performed using thrombin-activated human platelets and purified scFvs. Resting platelets and an irrelevant scFv, isolated from the same library, were used as negative controls. Expression of TLT-1 on the surface of the activated platelets was detected using the anti-TLT-1 pAb. The six anti-TLT-1 scFvs reacted to a different extent with activated platelets, as shown in FIG. 4A. Strong to moderate reactivity with activated platelets was found with clones C10, A7, D1 and A1, while scFv B8 and A8 only weakly reacted with TLT-1 on platelets. No binding of the negative control scFv was detected to resting and to activated platelets (FIGS. 4A and 4B). All scFvs demonstrated minimal binding on resting platelets, consistent with the low level of TLT-1 on the surface of these cells. A representative histogram of binding to resting platelets compared to activated platelets is shown for scFv C10 in FIG. 4B.

Based on these results, the scFv that showed the highest binding activity to activated platelets compared to controls was C10. Moreover, the scFv C10 performed better than the commercially available pAb anti-TLT-1 (FIG. 4B). Therefore, scFv C10 was used to perform an immunoprecipitation of TLT-1 from whole cell lysates of resting and activated platelets. The scFv C10 efficiently immunoprecipitated TLT-1 from both cell lysates, as shown in the western blot analysis of the immunoprecipitates probed with anti-hTLT-1 pAb (FIG. 4C). The two major bands of 35 and 25 kDa detected in the western blot analysis of platelet lysate were both present in scFv C10 immunoprecipitates, while no bands were detected in the control immunoprecipitate. FIG. 4D shows flow cytometric analysis of scFvs C10 and D1 compared to an irrelevant scFv, which was used as the control.

Taken together, these data confirm the identification of scFvs highly specific for TLT-1, and that some of these antibodies readily react with TLT-1 in platelets.

Example 5

Inhibition of Thrombin-Mediated Platelet Aggregation by Using Anti-TLT-1 scFvs

Initially, platelet aggregation was evaluated using a commercially available anti-TLT-1 pAb. Platelets were incubated with anti-TLT-1 pAb, anti-TREM-1 pAb as an isotype control, or vehicle alone, then added thrombin (0.125 U/ml) and the aggregation response was measured. Addition of anti-TLT-1 pAb gave only a slight increase in thrombin-mediated aggregation relative to controls, as shown in FIG. 5A). This initial observation suggested that the pAb might not react with relevant epitopes on TLT-1. Therefore, the isolated anti-TLT-1 scFvs were tested in the same assay. When thrombin was used as an agonist, there was a significant inhibition of aggregation by scFv C10. This inhibition was not observed using the vehicle alone and the negative control scFv (FIG. 5B). After thrombin stimulation, scFv C10-treated platelets underwent initial shape change as evidenced by the immediate increase, followed by a gradual decrease in absorbance. Primary aggregation was potently suppressed in each of several donors (n=6). In most samples, platelets treated with scFv C10 before the addition of thrombin finally aggregated after approximately 15-20 minutes (data not shown). ScFv C10 did not inhibit PMA-induced aggregation (FIG. 5C), suggesting that the TLT-1 effect can be bypassed by direct protein kinase C activation, and that blockade of TLT-1 did not destroy the potential of platelets to respond. ScFv C10-mediated inhibition was concentration-dependent as shown in FIG. 5D. Concentrations of 1.5-3 µg/ml were ineffective, whereas a concentration of 6 µg/ml gave a near maximum inhibition. Next whether scFv C10 could inhibit collagen-induced aggregation was addressed in parallel experiments. Collagen concentrations from 1-10 µg/ml resulted in only negligible changes in the aggregation curves when comparing TLT-1 specific scFvs with vehicle or negative controls (FIG. 5E and data not shown). FIG. 5E shows the platelet response to 5 µg/ml collagen after incubation with scFv C10 at 12 µg/ml. Taken together these results suggest that interference with TLT-1 affects a pathway involved in thrombin, but not collagen or PMA-induced aggregation. FIG. 5F shows that increasing concentrations of thrombin overcome C10-mediated inhibition of aggregation. ScFv A1 and A8 in the same assay showed an inhibitory effect on platelet aggregation, similar to scFv C10 (data not shown). However, scFvs A7, B8, and D1 at the same concentration of scFv C10 (FIG. 5G) or greater (data not shown) had no significant effect on platelet aggregation, as shown by the representative curve for scFv D1. This result could been explained by the amino acid sequence variability found in the CDR1 and CDR2 of the scFvs, which may imply that these antibodies either bind different epitopes on TLT-1 or similar epitopes with different affinities (as shown in Table 1, above). Nevertheless, it is important to note that interference with TLT-1 inhibited thrombin-mediated aggregation but not that induced by collagen or ADP. TLT-1 is an ITIM containing receptor demonstrated to bind SHP-1 and/or SHP-2 (12). Classical models of ITIM-mediated inhibition would suggest that TLT-1 might inhibit an ITAM containing, phosphotyrosine-based receptor system such as the collagen receptor GPVI, which signals via FcRγ. In addition, most models of inhibitory signaling require co-clustering of the inhibitory and target receptors to promote inhibitory signaling. ScFvs are small, monovalent molecules, making co-clustering unlikely. It cannot be ruled out, however, that at high enough concentrations, the scFv engages enough TLT-1 molecules to send an inhibition signal.

Example 6

TLT-1, found in the a-granules of resting platelets, is translocated to the platelet surface following activation by thrombin (Washington et al. Blood 2004). A time course experiment was performed using resting and activated mouse platelets to characterize activation dependent changes in mTLT-1 expression. Following activation, platelet suspensions were combined with an equal volume of 2× lysis buffer. The equivalent of $1.5 \times 10^7$ platelets was resolved by polyacrylamide gel electrophoresis. During the 5-hour period, the apparent mass of mTLT-1 shifted from almost exclusively a 40-kD form to a nearly equal mixture of 40 kD and 25-kD forms (FIG. 7A). This observation led next to the testing of whether the smaller mTLT-1 isoform was released from platelets. In subsequent experiments, platelets were centrifuged prior to lysis to separate the cell-associated and soluble fractions. Pelleted resting platelets and the resulting supernatant showed no trace of a 25-kD isoform, as shown in FIG. 7B, Lanes 1 and 2. However, following activation with thrombin, a soluble form of mTLT-1 could be detected in the supernatant after removal of platelets by centrifugation (FIG. 7B, Lane 4). The 25-kD form of mTLT-1 was detected in murine serum when probed with an antibody specific for the extracellular domain of mTLT-1, but not detected in serum using an antibody specific to the cytoplasmic domain of mTLT-1, suggesting that the species in serum includes the extracellular domain (FIG. 7C). The identity of the 25 KDa band was confirmed as TLT-1 by showing that two different antibodies directed toward the extracellular domain of mTLT-1 reacted with it, whereas a series of control antibodies did not, as shown in FIG. 7D. TLT-1 was not observed in murine plasma nor in defibrinated plasma (FIG. 7D, Lanes 2, 3). To test whether mTLT-1 found in serum resulted from proteolytic cleavage of the platelet surface-associated variant, or from alternative transcription of soluble isoforms, HEK293 cells were transfected with cDNA encoding mTLT-1, or a mTLT1/YFP chimera, as shown in FIG. 7E. Similar results were obtained for both forms of recombinant mTLT-1 in that the protein is observed near the expected molecular masses in the cell-associated fractions (Lanes 1, 3) and isoforms of identical size were detected in conditioned cell media, irrespective of the cDNA construct used for transfection (Lanes 2, 4). The isoform released from HEK293 cells was identical in apparent molecular mass to the form detected in murine serum (Lane 5).

Although there is greater than 70% homology between the murine and human orthologs, the experiments were repeated using human platelets, serum, and HEK293 cells that were transfected with hTLT-1 cDNA. Human platelets and serum probed with an antibody specific for the extracellular domain of hTLT-1 demonstrate similarities to the murine system (FIGS. 8A and 8B). Activated human platelets show various hTLT-1 isoforms, but human serum contains only a pair of smaller forms (FIG. 8A). In human serum, two bands corresponding to apparent masses of 12 and 14 kD were observed, as shown in FIG. 8A, very similar to the doublet observed in supernatant following platelet activation, as shown in FIG. 8B). Human TLT-1 is absent from supernatants of resting platelets and from plasma (FIG. 8B). To test whether hTLT-1 fragments were in fact derived from cleavage of hTLT-1, or from alternative transcription, HEK293 cells were transfected with the hTLT-1 cDNA encoding the smaller of two known forms of hTLT-1, and then the cell culture media was evaluated for the presence of these fragments. No hTLT-1 was detected from wild-type HEK293 cells or conditioned culture media, but full length (35 kDa) and smaller forms (12 and 14 kDa) are clearly observed in extracts from cells which were transfected with the hTLT-1 gene, as shown in FIG. 8C. Lanes 4 and 5 of FIG. 8C show that the isoforms of recombinant hTLT-1 released from HEK293 cells (Lane 4) are identical in apparent molecular mass to those released from platelets following activation with thrombin (Lane 5).

Taken together, the experiments described herein examining TLT-1 from platelets and recombinant TLT-1 from HEK293 cells suggest that the extracellular domain may have a function independent of the intact molecule.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. All patents and publications mentioned in this specification are herein incorporated by reference to the same extent as if each independent patent and publication was specifically and individually indicated to be incorporated by reference.

REFERENCES

1. Ruggeri Z M. Platelets in atherothrombosis. Nat Med 2002; 8: 1227-34.
2. Burke A P, Farb A, Malcom G T, Liang Y H, Smialek J, Virmani R. Coronary risk factors and plaque morphology in men with coronary disease who died suddenly. N Engl J Med 1997; 336: 1276-82.
3. Virmani R, Kolodgie F D, Burke A P, Farb A, Schwartz S M. Lessons from sudden coronary death: a comprehensive morphological classification scheme for atherosclerotic lesions. Arterioscler Thromb Vasc Biol 2000; 20: 1262-75.
4. Phillips D R, Conley P B, Sinha U, Andre P. Therapeutic approaches in arterial thrombosis. J Thromb Haemost 2005; 3: 1577-89.
5. Nieswandt B, Aktas B, Moers A, Sachs U J. Platelets in atherothrombosis: lessons from mouse models. J Thromb Haemost 2005; 3: 1725-36.
6. A randomised, blinded, trial of clopidogrel versus aspirin in patients at risk of ischaemic events (CAPRIE). CAPRIE Steering Committee. Lancet 1996; 348: 1329-39.
7. Popma J J, Satler L F. Early and late clinical outcome following coronary angioplasty performed with platelet glycoprotein IIb/IIIa receptor inhibition: the EPIC Trial results. J Invasive Cardiol 1994; 6 Suppl A: 19A-28A.
8. Genetta T B, Mauro V F. ABCIXIMAB: a new antiaggregant used in angioplasty. Ann Pharmacother 1996; 30: 251-7.
9. Washington A V, Quigley L, McVicar D W. Initial characterization of TREM-like transcript (TLT)-1: a putative inhibitory receptor within the TREM cluster. Blood 2002; 100: 3822-4.
10. Washington A V, Schubert R L, Quigley L, Disipio T, Feltz R, Cho E H, McVicar D W. A TREM family member, TLT-1, is found exclusively in the alpha-granules of megakaryocytes and platelets. Blood 2004; 104: 1042-7.
11. Radaev S, Kattah M, Rostro B, Colonna M, Sun P D. Crystal structure of the human myeloid cell activating receptor TREM-1. Structure 2003; 11: 1527-35.
12. Barrow A D, Astoul E, Floto A, Brooke G, Relou I A, Jennings N S, Smith K G, Ouwehand W, Farndale R W, Alexander D R, Trowsdale J. Cutting edge: TREM-like transcript-1, a platelet immunoreceptor tyrosine-based inhibition motif encoding costimulatory immunoreceptor that enhances, rather than inhibits, calcium signaling via SHP-2. J Immunol 2004; 172: 5838-42.
13. Winter G, Griffiths A D, Hawkins R E, Hoogenboom H R. Making antibodies by phage display technology. Annu Rev Immunol 1994; 12: 433-55.
14. McCafferty J, Griffiths A D, Winter G, Chiswell D J. Phage antibodies: filamentous phage displaying antibody variable domains. Nature 1990; 348: 552-4.
15. Bird R E, Hardman K D, Jacobson J W, Johnson S, Kaufman B M, Lee S M, Lee T, Pope S H, Riordan G S, Whitlow M. Single-chain antigen-binding proteins. Science 1988; 242: 423-6.
16. Laffly E, Sodoyer R. Monoclonal and recombinant antibodies, 30 years after . . . . Hum Antibodies 2005; 14: 33-55.
17. Griffiths A D, Malmqvist M, Marks J D, Bye J M, Embleton M J, McCafferty J, Baier M, Holliger K P, Gorick B D, Hughes-Jones N C, Human anti-self antibodies with high specificity from phage display libraries. EMBO J 1993; 12: 725-34.
18. Goletz S, Christensen P A, Kristensen P, Blohm D, Tomlinson I, Winter G, Karsten U. Selection of large diversities of antiidiotypic antibody fragments by phage display. J Mol Biol 2002; 315: 1087-97.
19. Yan J P, Ko J H, Qi Y P. Generation and characterization of a novel single-chain antibody fragment specific against human fibrin clots from phage display antibody library. Thromb Res 2004; 114: 205-11.
20. Liu Z X, Yi G H, Qi Y P, Liu Y L, Yan J P, Qian J, Du E Q, Ling W F. Identification of single-chain antibody fragments specific against SARS-associated coronavirus from phage-displayed antibody library. Biochem Biophys Res Commun 2005; 329: 437-44.
21. Paul S P, Taylor L S, Stansbury E K, McVicar D W. Myeloid specific human CD33 is an inhibitory receptor with differential ITIM function in recruiting the phosphatases SHP-1 and SHP-2. Blood 2000; 96: 483-90.
22. Gattis J L, Washington A V, Chisholm M M, Quigley L, Szyk A, McVicar D W, Lubkowski J. The structure of the extracellular domain of triggering receptor expressed on myeloid cells like transcript-1, and evidence for a naturally occurring soluble fragment. J Biol Chem 2006; 281: 13396-403.
23. Hoogenboom H R, Winter G. By-passing immunisation. Human antibodies from synthetic repertoires of germline VH gene segments rearranged in vitro. J Mol Biol 1992; 227: 381-8.
24. Vaughan T J, Williams A J, Pritchard K, Osbourn J K, Pope A R, Earnshaw J C, McCafferty J, Hodits R A, Wilton J, Johnson K S. Human antibodies with sub-nanomolar affinities isolated from a large non-immunized phage display library. Nat Biotechnol 1996; 14: 309-14.
25. Miller K D, Weaver-Feldhaus J, Gray S A, Siegel R W, Feldhaus M J. Production, purification, and characterization of human scFv antibodies expressed in *Saccharomyces cerevisiae*, *Pichia pastoris*, and *Escherichia coli*. Protein Expr Purif 2005; 42: 255-67.
26. Feldhaus M J, Siegel R W. Yeast display of antibody fragments: a discovery and characterization platform. J Immunol Methods 2004; 290: 69-80.
27. McNicol A, Israels S J. Platelets and anti-platelet therapy. J Pharmacol Sci 2003; 93: 381-96.
28. Schwarz M, Rottgen P, Takada Y, Le G F, Knackmuss S, Bassler N, Buttner C, Little M, Bode C, Peter K. Single-chain antibodies for the conformation-specific blockade of activated platelet integrin alphaIIbbeta3 designed by subtractive selection from naive human phage libraries. FASEB J 2004; 18: 1704-6.

29. Hagay Y, Lahav J, Levanon A, Panet A. Function-modulating human monoclonal antibodies against platelet-membrane receptors isolated from a phage-display library. J Thromb Haemost 2003; 1: 1829-36.
30. Dai K, Zhu H, Ruan C. Generation and characterization of recombinant single chain Fv antibody that recognizes platelet glycoprotein Ibalpha. Thromb Res 2003; 109: 137-44.
31. Holliger P, Hudson P J. Engineered antibody fragments and the rise of single domains. Nat Biotechnol 2005; 23: 1126-36.
32. Gibot S, Kolopp-Sarda M N, Bene M C, Bollaert P E, Lozniewski A, Mory F, Levy B, Faure G C. A soluble form of the triggering receptor expressed on myeloid cells-1 modulates the inflammatory response in murine sepsis. J Exp Med 2004; 200: 1419-26.
33. King R G, Herrin B R, Justement L B. Trem-like transcript 2 is expressed on cells of the myeloid/granuloid and B lymphoid lineage and is up-regulated in response to inflammation. J immunol 2006; 176: 6012-21.
34. Moran N, Kiernan A, Dunne E, Edwards R J, Shields D C, Kenny D. Monitoring Modulators of platelet aggregation in a microtiter plate assay. Analy Biochem. 2006; 357: 77-84.
35. Vanhoorelbeke K., Ulrichts H, Schoolmeester A, Deckmyn H. Inhibition of platelet adhesion to collagen as a new target for antithrombotic drugs. Curr Drug Targets Cardiovasc Haematol Disord. 2003.3(2): 125-40.
36. Gibot S, Cravoisy A. Soluble Form of the Triggering Receptor Expressed on Myeloid Cells-1 as a Marker of Microbial Infection. Clin Med. Res. 2004. 2:181-187.
37. Gibot S, Le Renard P E, Bollaert P E et al. Surface triggering receptor expressed on myeloid cells 1 expression patterns in septic shock. Intensive Care Med. 2005. 31:594-597.
38. Chothia C, Lesk A M. Canonical structures for the hypervariable regions of immunoglobulins. J Mol Biol. 1987. 196:901-917.
39. Marutsuka K, Hatakeyama K, Yamashita A, Asada Y. Role of thrombogenic factors in the development of atherosclerosis. J Atheroscler Thromb. 2005; 12(1):1-8.
40. M. Monreal, A. W. A. Lensing, M. H. Prins, M. Bonet, J. Fernandez-Llamazares, J. Muchart, P. Prandoni and J. Angel Jiménez. Screening for occult cancer in patients with acute deep vein thrombosis or pulmonary embolism. Journal of Thrombosis and Haemostasis. 2004. 2: 876.

What is claimed is:

1. A single chain anti-TREM-like transcript-1 (TLT-1) antibody or a functional fragment thereof, encoded by the nucleic acids selected from the group consisting of: SEQ ID NO: 1, SEQ ID NO: 2 and SEQ ID NO: 3, that has TLT-1 antigien specificity.

2. A pharmaceutical composition comprising a single chain anti-TLT-1 antibody or a functional fragment thereof and a pharmaceutically acceptable carrier, wherein the single chain anti-TLT-1 antibody or a functional fragment thereof, encoded by a nucleic acid sequence selected from SEQ ID NO: 1, SEQ ID NO: 2 or SEQ ID NO: 3, that has TLT-1 antigen specificity.

3. The pharmaceutical composition of claim 2, wherein the single chain anti-TLT-1 antibody or functional fragment thereof has specificity for the extracellular domain of TLT-1.

4. The pharmaceutical composition of claim 2, further comprising one or more therapeutic agents.

5. The pharmaceutical composition of claim 4, wherein the therapeutic agent is selected from the group consisting of: a chemotherapeutic agent, an anti-inflammatory agent, an antibiotic and an anticoagulant agent.

6. A kit comprising the single chain anti-TLT-1 antibody or a functional fragment thereof of claim 1 and instructions for use.

* * * * *